United States Patent
Qian et al.

(10) Patent No.: US 12,291,536 B2
(45) Date of Patent: May 6, 2025

(54) CRYSTAL FORM OF WEE1 INHIBITOR COMPOUND AND USE THEREOF

(71) Applicant: Wuxi Biocity Biopharmaceutics Co., Ltd., Jiangsu (CN)

(72) Inventors: Wenyuan Qian, Shanghai (CN); Chundao Yang, Shanghai (CN); Zhengwei Li, Shanghai (CN); Jie Li, Shanghai (CN); Jian Li, Shanghai (CN); Shuhui Chen, Shanghai (CN)

(73) Assignee: Wuxi Biocity Biopharmaceutics Co., Ltd., Jiangsu (CN)

( * ) Notice: Subject to any disclaimer, the term of this patent is extended or adjusted under 35 U.S.C. 154(b) by 796 days.

(21) Appl. No.: 17/607,447

(22) PCT Filed: Apr. 30, 2020

(86) PCT No.: PCT/CN2020/088451
§ 371 (c)(1),
(2) Date: Oct. 29, 2021

(87) PCT Pub. No.: WO2020/221358
PCT Pub. Date: Nov. 5, 2020

(65) Prior Publication Data
US 2022/0220120 A1    Jul. 14, 2022

(30) Foreign Application Priority Data

Apr. 30, 2019 (CN) .......................... 201910364694.X

(51) Int. Cl.
*C07D 487/22* (2006.01)

(52) U.S. Cl.
CPC ........ *C07D 487/22* (2013.01); *C07B 2200/13* (2013.01)

(58) Field of Classification Search
CPC .......................... C07D 487/22; C07B 2200/13
See application file for complete search history.

(56) References Cited

U.S. PATENT DOCUMENTS

| | | |
|---|---|---|
| 2005/0215556 A1 | 9/2005 | Lin et al. |
| 2009/0048275 A1 | 2/2009 | Beauchamps et al. |
| 2020/0325145 A1 | 10/2020 | Qian et al. |
| 2020/0377520 A1 | 12/2020 | Zhao et al. |

FOREIGN PATENT DOCUMENTS

| | | |
|---|---|---|
| CN | 108623615 A | 10/2018 |
| EP | 3875460 A1 | 9/2021 |
| RU | 2437885 C2 | 12/2011 |
| WO | 2007126122 A1 | 11/2007 |
| WO | 2008133866 A1 | 11/2008 |
| WO | 2013059485 A1 | 4/2013 |
| WO | 2017075629 A2 | 5/2017 |
| WO | 2019085933 A1 | 5/2019 |

OTHER PUBLICATIONS

Esposito F, Giuffrida R, Raciti G, Puglisi C, Forte S. Wee1 Kinase: A Potential Target to Overcome Tumor Resistance to Therapy. Int J Mol Sci. Oct. 1, 2021;22(19):10689. doi: 10.3390/ijms221910689. PMID: 34639030; PMCID: PMC8508993. (Year: 2021).*

Rao CV, Asch AS, Carr DJJ, Yamada HY. "Amyloid-beta accumulation cycle" as a prevention and/or therapy target for Alzheimer's disease. Aging Cell. Mar. 2020;19(3):e13109. doi: 10.1111/acel.13109. Epub Jan. 25, 2020. PMID: 31981470; PMCID: PMC7059149. (Year: 2020).*

Cecil Textbook of Medicine, 20th Ed, vol. 1, 1997 (Year: 1997).*

Gleeson MP, Hersey A, Montanari D, Overington J. Probing the links between in vitro potency, ADMET and physicochemical parameters. Nat Rev Drug Discov. Mar. 2011;10(3):197-208. doi: 10.1038/nrd3367. PMID: 21358739; PMCID: PMC6317702. (Year: 2011).*

Wu Q, Qian W, Sun X, Jiang S. Small-molecule inhibitors, immune checkpoint inhibitors, and more: FDA-approved novel therapeutic drugs for solid tumors from 1991 to 2021. J Hematol Oncol. Oct. 8, 2022;15(1):143. doi: 10.1186/s13045-022-01362-9. PMID: 36209184; PMCID: PMC9548212. (Year: 2022).*

Examination Report issued Mar. 24, 2023 in corresponding Indian Patent Application No. 202117053993.

Extended European Search Report issued Mar. 27, 2023 in corresponding EP Application No. 20798924.5.

Written Opinion issued May 1, 2023 in corresponding Singapore Application No. 11202111315X.

(Continued)

*Primary Examiner* — Alicia L Otton
(74) *Attorney, Agent, or Firm* — IceMiller LLP

(57) ABSTRACT

Disclosed is a crystal form of a compound of formula (I) and the use of the crystal form in the preparation of a drug for treating Wee1-related diseases.

Formula (I)

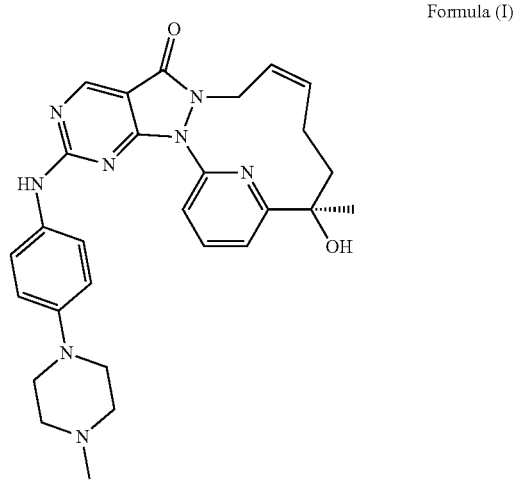

28 Claims, 9 Drawing Sheets

(56) References Cited

OTHER PUBLICATIONS

International Search Report mailed Aug. 12, 2020 in PCT/CN2020/088451.
Written Opinion mailed Aug. 12, 2020 in PCT/CN2020/088451.
Russian Office Action and Search Report issued Nov. 14, 2023 in corresponding RU application No. 2021134141.
Caira, Mino R., "Crystalline Polymorphism of Organic Compounds," Topics in Current Chemistry, vol. 198, pp. 163-208, Springer Verlag Berlin Heidelberg 1998.
Variankaval, Narayan, et al., "From Form to Function: Crystallization of Active Pharmaceutical Ingredients," American Institute of Chemical Engineers, vol. 54, No. 7, pp. 1682-1688, Jul. 2008.

* cited by examiner

CRYSTAL FORM OF WEE1 INHIBITOR COMPOUND AND USE THEREOF

CROSS-REFERENCE TO RELATED APPLICATION

This application is a Section 371 of International Application No. PCT/CN2020/088451 filed Apr. 30, 2020, which was published in the Chinese language Nov. 5, 2020, under International Publication No. WO 2020/221358 A1, which claims priority to Chinese Patent Application No. 201910364694.X filed Apr. 30, 2019, the disclosures of which are incorporated herein by reference in their entireties.

TECHNICAL FIELD

Disclosed are crystal forms of a compound of formula (I) and the use of the crystal forms for the manufacture of a medicament for treating a Wee1-related disease.

BACKGROUND

The cell cycle process is a complex process under the control of a series of cell cycle regulatory systems. The key of the cell cycle regulatory system is CDKs/Cyclins complex formed by the combination of cyclin-dependent kinases (CDKs) and cyclins (Cyclins). The complex can drive cells to enter the proliferation cycle, wherein the CDK1 (the human autoploid is also known as CDC2)/Cyclin B complex plays a key role in controlling cells into the M phase.

The DNA replication has to be completed before the cell enters the M phase. Due to the interference of various endogenous and exogenous factors, the mutations or damages often occur to the DNA. The abnormal DNA must be repaired, or it will cause mitotic disaster and cause cell death. The cell cycle checkpoint will cease the cell cycle and allow the repair of DNA before its entry of the M phase. The G1/S checkpoint at the end of the G1 phase and the G2/M checkpoint at the G2 phase are two main cell cycle checkpoints, which together are responsible for the recognition and repair of DNA damage. Normal cells utilize the G1/S checkpoint to complete DNA repair in the G1 phase, while nearly 50% of cancerous cells have defects in the tumor suppressor gene p53, rendering them lacking the G1/S checkpoint function. They have to rely more on the G2/M checkpoint to complete DNA repair. The G2/M checkpoint rarely undergoes mutations, making the cancer cells escape the treatment of DNA damaging agents and radiation.

Wee1 protein kinase is a cell cycle regulator, a member of the serine and threonine protein kinase family in the nucleus and is a key kinase for the G2/M checkpoint. The human "Wee" protein kinase family mainly includes Wee1 and Myt1, both of which can phosphorylate the Tyr15 site on CDC2, inhibit the activation of the CDC2/CyclinB complex, and block cells from entering the M phase until the DNA repair is completed. Myt1 can also phosphorylate the Thr14 site on CDC2, which is also a negative regulation of CDC2 activity. Wee1 kinase is highly expressed in many cancerous cells. By inhibiting Wee1 kinase, the tumor cells can be directly made to skip the DNA repair of G2 stage and enter mitosis in advance, which leads to tumor cell death, and achieve the purpose of treating cancer.

At present, a Wee1 inhibitor AZD1775 by AstraZeneca has entered the clinical phase II, and more than 30 clinical trials are under development, showing good therapeutic effects. AZD1775 was first developed by Merck, and therefore it is also known as MK-1775. In September 2013, Merck transferred the compound to AstraZeneca globally, and the relevant patents mainly include US20070254892, WO2007126122, EP2213673, WO2008133866, WO2011034743, etc. Abbott and Abbvie have also conducted research on Wee1 inhibitors, and relevant patents mainly include US2012220572, WO2013126656, WO2013012681, WO2013059485, WO2013013031, WO2013126656, etc. Almac's patents regarding Wee1 inhibitors include WO2014167347, WO2015019037, WO2015092431.

WO2008133866 discloses a compound of AZD1775 having the following structure:

AZD1775

SUMMARY

Provided is a Crystal Form A of a compound of formula (I), wherein the Crystal Form A has an X-ray powder diffraction (XRPD) pattern having characteristic diffraction peaks at the following 2θ angles: 5.71±0.2°, 12.68±0.2° and 15.32±0.2°.

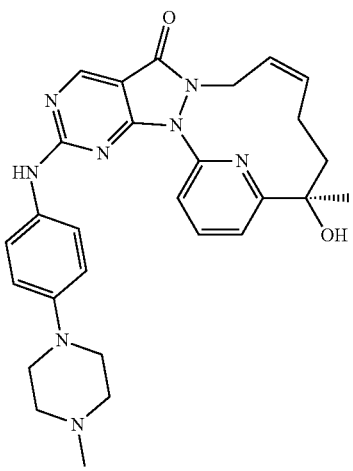

Formula (I)

In some embodiments according to the present disclosure, the Crystal Form A has an X-ray powder diffraction pattern having characteristic diffraction peaks at the following 2θ angles: 5.71±0.2°, 12.68±0.2°, 15.32±0.2°, 19.72±0.2°, 21.44±0.2°, 23.61±0.2° and 25.68±0.2°.

In some embodiments according to the present disclosure, the Crystal Form A has an X-ray powder diffraction pattern having characteristic diffraction peaks at the following 2θ angles: 5.71±0.2°, 12.68±0.2°, 15.32±0.2°, 18.04±0.2°, 19.72±0.2°, 21.44±0.2°, 23.61±0.2° and 25.68±0.2°.

In some embodiments according to the present disclosure, the Crystal Form A has an XRPD pattern as shown in FIG. 1.

In some embodiments according to the present disclosure, the Crystal Form A has an XRPD pattern with Analysis Data shown in Table 1:

TABLE 1

XRPD Pattern Analysis Data of Crystal Form A

| No. | 2θ angle (°) | Inter-planar spacing (Å) | Relative Intensity (%) |
|---|---|---|---|
| 1 | 5.046 | 17.4994 | 0.7 |
| 2 | 5.046 | 17.4994 | 0.7 |
| 3 | 5.711 | 15.4612 | 100 |
| 4 | 7.904 | 11.176 | 0.6 |
| 5 | 11.218 | 7.881 | 0.5 |
| 6 | 12.677 | 6.9773 | 27.4 |
| 7 | 14.71 | 6.0172 | 1.4 |
| 8 | 14.948 | 5.9216 | 0.8 |
| 9 | 15.318 | 5.7794 | 1.5 |
| 10 | 16.051 | 5.5173 | 0.5 |
| 11 | 17.159 | 5.1634 | 0.9 |
| 12 | 17.768 | 4.9877 | 0.5 |
| 13 | 18.043 | 4.9125 | 1 |
| 14 | 18.597 | 4.7672 | 0.4 |
| 15 | 18.906 | 4.69 | 0.9 |
| 16 | 19.719 | 4.4984 | 1.7 |
| 17 | 20.08 | 4.4184 | 0.4 |
| 18 | 20.413 | 4.3471 | 0.3 |
| 19 | 21.2 | 4.1874 | 0.6 |
| 20 | 21.435 | 4.142 | 2.1 |
| 21 | 21.669 | 4.0979 | 0.5 |
| 22 | 22.268 | 3.989 | 0.9 |
| 23 | 23.234 | 3.8252 | 0.8 |
| 24 | 23.607 | 3.7656 | 4.2 |
| 25 | 25.517 | 3.488 | 1.9 |
| 26 | 25.678 | 3.4665 | 2.2 |
| 27 | 26.043 | 3.4187 | 0.5 |
| 28 | 27.765 | 3.2104 | 0.4 |
| 29 | 28.007 | 3.1832 | 1 |
| 30 | 29.289 | 3.0467 | 0.4 |
| 31 | 30.426 | 2.9354 | 0.4 |

In some embodiments according to the present disclosure, the Crystal Form A has a Differential Scanning calorimetry curve (DSC) having one onset point of endothermic peak at 34.95±3° C., 174.75±3° C. and 219.12±3° C., respectively.

In some embodiments according to the present disclosure, the Crystal Form A has a DSC pattern as shown in FIG. 2.

In some embodiments according to the present disclosure, the Crystal Form A has a Thermogravimetric Analysis curve (TGA), wherein the weight loss at 70.33±3° C. is 0.7367%; and the weight loss at 209.42±3° C. is 3.123%.

In some embodiments according to the present disclosure, the Crystal Form A has a TGA pattern as shown in FIG. 3.

Provided is also a Crystal Form B of a compound of formula (I), wherein the Crystal Form B has an X-ray powder diffraction (XRPD) pattern having characteristic diffraction peaks at the following 2θ angles: 5.58±0.2°, 12.44±0.2° and 22.16±0.2°.

In some embodiments according to the present disclosure, the Crystal Form B has an X-ray powder diffraction pattern having characteristic diffraction peaks at the following 2θ angles: 5.58±0.2°, 11.71±0.2°, 12.44±0.2°, 14.48±0.2°, 15.13±0.2°, 18.64±0.2°, 22.16±0.2° and 26.33±0.2°.

In some embodiments according to the present disclosure, the Crystal Form B has an X-ray powder diffraction pattern having characteristic diffraction peaks at the following 2θ angles: 5.58±0.2°, 11.71±0.2°, 12.44±0.2°, 14.48±0.2°, 15.13±0.2°, 17.57±0.2°, 18.64±0.2°, 22.16±0.2° and 26.33±0.2°.

In some embodiments according to the present disclosure, the Crystal Form B has an XRPD pattern as shown in FIG. 4.

In some embodiments according to the present disclosure, the Crystal Form B has an XRPD pattern with Analysis Data shown in Table 2:

TABLE 2

XRPD Pattern Analysis Data of Crystal Form B

| No. | 2θ angle (°) | Inter-planar Spacing (Å) | Relative Intensity (%) |
|---|---|---|---|
| 1 | 5.577 | 15.8346 | 100 |
| 2 | 7.838 | 11.2705 | 1.1 |
| 3 | 9.807 | 9.0113 | 1.5 |
| 4 | 11.028 | 8.0162 | 2.4 |
| 5 | 11.713 | 7.549 | 6.4 |
| 6 | 12.056 | 7.3351 | 1.3 |
| 7 | 12.439 | 7.1098 | 30.4 |
| 8 | 13.706 | 6.4552 | 4.6 |
| 9 | 14.233 | 6.2177 | 2.9 |
| 10 | 14.476 | 6.1138 | 5.7 |
| 11 | 15.127 | 5.8522 | 5.8 |
| 12 | 16.717 | 5.2989 | 1.1 |
| 13 | 17.146 | 5.1674 | 1.2 |
| 14 | 17.567 | 5.0443 | 7.7 |
| 15 | 18.241 | 4.8596 | 2 |
| 16 | 18.637 | 4.757 | 6.5 |
| 17 | 19.582 | 4.5295 | 4.3 |
| 18 | 20.016 | 4.4325 | 5.3 |
| 19 | 21.831 | 4.0677 | 3.2 |
| 20 | 22.164 | 4.0075 | 18.7 |
| 21 | 23.018 | 3.8607 | 2.8 |
| 22 | 23.626 | 3.7626 | 2.1 |
| 23 | 25.007 | 3.5579 | 2.3 |
| 24 | 25.261 | 3.5227 | 1.4 |
| 25 | 25.808 | 3.4493 | 1.3 |
| 26 | 26.327 | 3.3824 | 8.5 |
| 27 | 28.535 | 3.1255 | 1 |
| 28 | 30.939 | 2.8879 | 0.9 |
| 29 | 31.076 | 2.8755 | 0.9 |
| 30 | 32.083 | 2.7875 | 0.7 |
| 31 | 34.201 | 2.6196 | 0.7 |

In some embodiments according to the present disclosure, the Crystal Form B has a Differential Scanning calorimetry curve (DSC) having one onset point of endothermic peak at 42.88±3° C., 198.79±3° C. and 222.36±3° C., respectively.

In some embodiments according to the present disclosure, the Crystal Form B has a DSC pattern as shown FIG. 5.

In some embodiments according to the present disclosure, the Crystal Form B has a Thermogravimetric Analysis curve (TGA), wherein the weight loss at 64.21±3° C. is 3.265%; and the weight loss at 243.05±3° C. is 1.516%.

In some embodiments according to the present disclosure, the Crystal Form B has a TGA pattern as shown in FIG. 6.

Provided is also a Crystal Form C of a compound of formula (I), wherein the Crystal Form C has an X-ray powder diffraction (XRPD) pattern having characteristic diffraction peaks at the following 2θ angles: 5.05±0.2°, 5.58±0.2° and 12.44±0.2°.

In some embodiments according to the present disclosure, the Crystal Form C has an X-ray powder diffraction pattern having characteristic diffraction peaks at the following 2θ angles: 5.05±0.2°, 5.58±0.2°, 12.44±0.2°, 15.91±0.2°, 16.68±0.2°, 17.61±0.2°, 22.19±0.2° and 26.37±0.2°.

In some embodiments according to the present disclosure, the Crystal Form C has an XRPD pattern as shown in FIG. 7.

In some embodiments according to the present disclosure, the Crystal Form C has an XRPD pattern with Analysis Data shown in Table 3:

TABLE 3

XRPD Pattern Analysis Data of Crystal Form C

| No. | 2θ angle (°) | Inter-planar spacing (Å) | Relative Intensity (%) |
|---|---|---|---|
| 1 | 5.047 | 17.4944 | 12.4 |
| 2 | 5.577 | 15.8334 | 100 |
| 3 | 10.945 | 8.077 | 0.6 |
| 4 | 11.137 | 7.9381 | 1.4 |
| 5 | 11.712 | 7.5495 | 1.2 |
| 6 | 12.438 | 7.1105 | 12.8 |
| 7 | 13.726 | 6.4461 | 0.6 |
| 8 | 14.221 | 6.2226 | 0.8 |
| 9 | 14.496 | 6.1055 | 0.9 |
| 10 | 15.126 | 5.8527 | 1.1 |
| 11 | 15.911 | 5.5654 | 6.4 |
| 12 | 16.108 | 5.4978 | 2.8 |
| 13 | 16.685 | 5.309 | 3.3 |
| 14 | 17.61 | 5.0322 | 2.6 |
| 15 | 17.921 | 4.9455 | 0.4 |
| 16 | 18.694 | 4.7427 | 2.2 |
| 17 | 19.6 | 4.5254 | 0.8 |
| 18 | 20.032 | 4.4288 | 0.7 |
| 19 | 21.275 | 4.1728 | 0.5 |
| 20 | 21.436 | 4.1418 | 0.7 |
| 21 | 21.869 | 4.0608 | 0.8 |
| 22 | 22.186 | 4.0036 | 6.1 |
| 23 | 23.035 | 3.8578 | 1.8 |
| 24 | 23.627 | 3.7626 | 0.9 |
| 25 | 24.832 | 3.5826 | 0.3 |
| 26 | 25.002 | 3.5586 | 0.6 |
| 27 | 25.278 | 3.5203 | 0.5 |
| 28 | 26.367 | 3.3773 | 3 |
| 29 | 26.98 | 3.302 | 0.4 |
| 30 | 28.633 | 3.1151 | 0.2 |
| 31 | 28.939 | 3.0828 | 0.4 |
| 32 | 34.293 | 2.6127 | 0.2 |

In some embodiments according to the present disclosure, the Crystal Form C has a Differential Scanning calorimetry curve (DSC) having one onset point of endothermic peak at 37.06±3° C., 189.16±3° C. and 218.61±3° C., respectively.

In some embodiments according to the present disclosure, the Crystal Form C has a DSC pattern as shown in FIG. 8.

In some embodiments according to the present disclosure, the Crystal Form C has a Thermogravimetric Analysis curve (TGA), wherein the weight loss at 64.98±3° C. is 2.211%; and the weight loss at 224.71±3° C. is 1.127%.

In some embodiments according to the present disclosure, the Crystal Form C has a TGA pattern as shown in FIG. 9.

Provided is also a Crystal Form D of a compound of formula (I), wherein the Crystal Form D has an X-ray powder diffraction (XRPD) pattern having characteristic diffraction peaks at the following 2θ angles: 5.22±0.2°, 15.99±0.2° and 16.57±0.2°.

In some embodiments according to the present disclosure, the Crystal Form D has an X-ray powder diffraction pattern having characteristic diffraction peaks at the following 2θ angles: 5.22±0.2°, 15.99±0.2°, 16.57±0.2° and 21.22±0.2°.

In some embodiments according to the present disclosure, the Crystal Form D has an X-ray powder diffraction pattern having characteristic diffraction peaks at the following 2θ angles: 5.22±0.2°, 15.18±0.2°, 15.99±0.2°, 16.57±0.2°, 17.08±0.2°, 18.60±0.2°, 21.22±0.2° and 21.89±0.2°.

In some embodiments according to the present disclosure, the Crystal Form D has an X-ray powder diffraction pattern having characteristic diffraction peaks at the following 2θ angles: 5.22±0.2°, 15.18±0.2°, 15.99±0.2°, 16.57±0.2°, 17.08±0.2°, 17.90±0.2°, 18.60±0.2°, 21.22±0.2°, 21.89±0.2°, 25.24±0.2° and 27.00±0.2°.

In some embodiments according to the present disclosure, the Crystal Form D has an XRPD pattern as shown in FIG. 10.

In some embodiments according to the present disclosure, the Crystal Form D has an XRPD pattern with Analysis Data shown in Table 4:

TABLE 4

XRPD Pattern Analysis Data of of Crystal Form D

| No. | 2θ angle (°) | Inter-planar spacing (Å) | Relative Intensity (%) |
|---|---|---|---|
| 1 | 5.224 | 16.9027 | 100 |
| 2 | 10.424 | 8.4794 | 4 |
| 3 | 12.774 | 6.9241 | 1.9 |
| 4 | 15.18 | 5.8316 | 7.9 |
| 5 | 15.595 | 5.6774 | 22.3 |
| 6 | 15.992 | 5.5373 | 58.7 |
| 7 | 16.567 | 5.3466 | 18.1 |
| 8 | 17.075 | 5.1886 | 15.3 |
| 9 | 17.904 | 4.9503 | 4.9 |
| 10 | 18.201 | 4.87 | 5.1 |
| 11 | 18.599 | 4.7668 | 12.1 |
| 12 | 19.506 | 4.5472 | 4.1 |
| 13 | 21.22 | 4.1834 | 25.5 |
| 14 | 21.888 | 4.0573 | 4.8 |
| 15 | 22.936 | 3.8743 | 1.6 |
| 16 | 25.242 | 3.5253 | 8.2 |
| 17 | 26.048 | 3.418 | 3.5 |
| 18 | 26.609 | 3.3472 | 2 |
| 19 | 26.997 | 3.3 | 7.6 |
| 20 | 27.492 | 3.2417 | 2.9 |
| 21 | 28.517 | 3.1274 | 1.6 |
| 22 | 29.898 | 2.986 | 3.5 |
| 23 | 30.55 | 2.9238 | 3.8 |
| 24 | 31.333 | 2.8525 | 2 |
| 25 | 32.348 | 2.7653 | 1.7 |
| 26 | 32.95 | 2.7161 | 1.3 |
| 27 | 34.522 | 2.596 | 1.9 |
| 28 | 34.545 | 2.5943 | 2 |
| 29 | 36.655 | 2.4496 | 2.1 |
| 30 | 39.522 | 2.2783 | 1.7 |

In some embodiments according to the present disclosure, the Crystal Form D has a Differential Scanning calorimetry curve (DSC) having one onset point of endothermic peak at 56.07±3° C., 193.93±3° C. and 216.54±3° C., respectively.

In some embodiments according to the present disclosure, the Crystal Form D has a Differential Scanning calorimetry curve (DSC) having one onset point of endothermic peak at 56.07±3° C., 193.93±3° C. and 216.54±3° C., respectively; and one peak value of exothermic peak at 206.82±3° C.

In some embodiments according to the present disclosure, the Crystal Form D has a DSC pattern as shown in FIG. 11.

In some embodiments according to the present disclosure, the Crystal Form D has a Thermogravimetric Analysis curve (TGA), wherein the weight loss at 79.35±3° C. is 1.977%; and the weight loss at 223.66±3° C. is 1.589%.

In some embodiments according to the present disclosure, the Crystal Form D has a TGA pattern as shown in FIG. 12.

Provided is also a Crystal Form E of a compound of formula (I), wherein the Crystal Form E has an X-ray powder diffraction (XRPD) pattern having characteristic diffraction peaks at the following 2θ angles: 8.65±0.2°, 14.22±0.2° and 24.58±0.2°.

In some embodiments according to the present disclosure, the Crystal Form E has an X-ray powder diffraction pattern having characteristic diffraction peaks at the following 2θ angles: 8.65±0.2°, 11.41±0.2°, 13.13±0.2°, 14.22±0.2°, 17.35±0.2°, 18.34±0.2°, 20.39±0.2°, 20.94±0.2° and 24.58±0.2°.

In some embodiments according to the present disclosure, the Crystal Form E has an XRPD pattern as shown in FIG. 13.

In some embodiments according to the present disclosure, the Crystal Form E has an XRPD pattern with Analysis Data shown in Table 5:

TABLE 5

XRPD Pattern Analysis Data of Crystal Form E

| No. | 2θ angle (°) | Inter-planar spacing (Å) | Relative Intensity (%) |
|---|---|---|---|
| 1 | 6.507 | 13.5715 | 8.8 |
| 2 | 8.653 | 10.2107 | 100 |
| 3 | 11.414 | 7.7457 | 15.2 |
| 4 | 13.132 | 6.7365 | 26.9 |
| 5 | 14.217 | 6.2247 | 66.8 |
| 6 | 16.211 | 5.4632 | 4.5 |
| 7 | 17.354 | 5.1058 | 16.5 |
| 8 | 18.065 | 4.9065 | 4.8 |
| 9 | 18.341 | 4.8332 | 18.1 |
| 10 | 18.974 | 4.6733 | 1.8 |
| 11 | 20.39 | 4.3518 | 22.8 |
| 12 | 20.941 | 4.2386 | 23.4 |
| 13 | 21.594 | 4.1119 | 9.6 |
| 14 | 22.169 | 4.0065 | 5.5 |
| 15 | 22.68 | 3.9174 | 9.9 |
| 16 | 22.954 | 3.8713 | 4 |
| 17 | 23.173 | 3.8352 | 2.8 |
| 18 | 24.575 | 3.6195 | 28.2 |
| 19 | 25.243 | 3.5252 | 11 |
| 20 | 26.188 | 3.4001 | 6.7 |
| 21 | 26.428 | 3.3697 | 6.9 |
| 22 | 26.882 | 3.3139 | 1.7 |
| 23 | 28.358 | 3.1446 | 5.4 |
| 24 | 28.612 | 3.1173 | 2.2 |
| 25 | 30.409 | 2.937 | 5.5 |
| 26 | 31.1 | 2.8733 | 1.9 |
| 27 | 31.688 | 2.8213 | 2.9 |
| 28 | 32.322 | 2.7674 | 1.6 |
| 29 | 32.874 | 2.7222 | 1.6 |
| 30 | 33.876 | 2.6439 | 2 |
| 31 | 34.711 | 2.5822 | 2.2 |
| 32 | 35.02 | 2.5602 | 1.6 |

In some embodiments according to the present disclosure, the Crystal Form E has a Differential Scanning calorimetry curve (DSC) having one onset point of endothermic peak at 121.57±3° C., 197.26±3° C. and 217.23±3° C., respectively; and one peak value of exothermic peak at 168.31±3° C. and 212.95±3° C., respectively.

In some embodiments according to the present disclosure, the Crystal Form E has a DSC pattern as shown in FIG. 14.

In some embodiments according to the present disclosure, the Crystal Form E has a Thermogravimetric Analysis curve (TGA), wherein the weight loss at 143.31±3° C. is 6.775%; and the weight loss at 213.62±3° C. is 0.3184%.

In some embodiments according to the present disclosure, the Crystal Form E has a TGA pattern as shown in FIG. 15.

Provided is also a Crystal Form F of a compound of formula (I), wherein the Crystal Form F has an X-ray powder diffraction (XRPD) pattern having characteristic diffraction peaks at the following 2θ angles: 5.06±0.2°, 15.91±0.2° and 16.68±0.2°.

In some embodiments according to the present disclosure, the Crystal Form F has an X-ray powder diffraction pattern having characteristic diffraction peaks at the following 2θ angles: 5.06±0.2°, 8.34±0.2°, 10.98±0.2°, 15.13±0.2°, 15.91±0.2°, 16.68±0.2°, 17.63±0.2° and 18.87±0.2°.

In some embodiments according to the present disclosure, the Crystal Form F has an X-ray powder diffraction pattern having characteristic diffraction peaks at the following 2θ angles: 5.06±0.2°, 8.34±0.2°, 10.98±0.2°, 15.13±0.2°, 15.91±0.2°, 16.68±0.2°, 17.63±0.2°, 18.87±0.2°, 20.33±0.2°, 21.44±0.2°, 22.01±0.2°, 24.04±0.2°, 25.32±0.2° and 25.66±0.2°.

In some embodiments according to the present disclosure, the Crystal Form F has an XRPD pattern as shown in FIG. 16.

In some embodiments according to the present disclosure, the Crystal Form F has an XRPD pattern with Analysis Data shown in Table 6:

TABLE 6

XRPD Pattern Analysis Data of Crystal Form F

| No. | 2θ angle (°) | Inter-planar spacing (Å) | Relative Intensity (%) |
|---|---|---|---|
| 1 | 5.062 | 17.4414 | 100 |
| 2 | 8.341 | 10.5913 | 3.3 |
| 3 | 10.077 | 8.7708 | 1.8 |
| 4 | 10.98 | 8.0515 | 4.7 |
| 5 | 15.128 | 5.8518 | 6.1 |
| 6 | 15.911 | 5.5653 | 59 |
| 7 | 16.685 | 5.3089 | 30 |
| 8 | 17.628 | 5.027 | 12 |
| 9 | 17.945 | 4.939 | 1.8 |
| 10 | 18.869 | 4.6992 | 2.6 |
| 11 | 19.719 | 4.4983 | 0.9 |
| 12 | 20.332 | 4.3641 | 4 |
| 13 | 21.44 | 4.1411 | 5.3 |
| 14 | 22.006 | 4.0358 | 3.2 |
| 15 | 23.328 | 3.81 | 1.2 |
| 16 | 23.898 | 3.7204 | 2.7 |
| 17 | 24.181 | 3.6776 | 3 |
| 18 | 25.325 | 3.5139 | 3.1 |
| 19 | 25.656 | 3.4694 | 2.5 |
| 20 | 26.96 | 3.3045 | 1.2 |
| 21 | 27.271 | 3.2674 | 1.9 |
| 22 | 29.026 | 3.0738 | 1.8 |
| 23 | 32.834 | 2.7254 | 0.8 |
| N/A | | | |

In some embodiments according to the present disclosure, the Crystal Form F has a Differential Scanning calorimetry curve (DSC) having one onset point of endothermic peak at 48.69±3° C. and 225.26±3° C., respectively.

In some embodiments according to the present disclosure, the Crystal Form F has a DSC pattern as shown in FIG. 17.

In some embodiments according to the present disclosure, the Crystal Form F has a Thermogravimetric Analysis curve (TGA), wherein the weight loss at 100±3° C. is 3.404%.

In some embodiments according to the present disclosure, the Crystal Form F has a TGA pattern as shown in FIG. 18.

Provided is further a process for preparing a Crystal Form F of a compound of formula (I), comprising,
 (a) adding the compound of formula (I) into an alcohol solvent with stirring which is heated in an oil bath to 55~65° C.;
 (b) stirring at 47° C.-53° C. for 72 h;
 (c) stopping heating and keeping stirring with the temperature spontaneously lowered for 1 h to 27° C.;
 (d) allowing standing for 18 h, filtering and rinsing the filter cake with methanol;
 (e) drying under vacuum at 60° C. for 48 h.

In some embodiments according to the present disclosure, the alcohol solvent is methanol.

Provided is further use of the Crystal Form A, the Crystal Form B, the Crystal Form C, the Crystal Form D, the Crystal Form E, or the Crystal Form F for the manufacture of a medicament for treating a Wee1-related disease.

Technical Effect

The Crystal Form A, Crystal Form B, Crystal Form C, Crystal Form D, Crystal Form E and Crystal Form F of the compound according to the present disclosure have good stability, are less effected by light, heat and humidity, have high solubility and promising druggability.

Definition

Unless stated otherwise, the following terms and phrases have the following definitions. A specific term or phrase should not be considered as indefinite or unclear without specific definition and should be understood according to the normal meanings. A tradename used herein shall refer to the corresponding article or the active ingredient.

The intermediate compounds herein can be prepared by various synthesis processes well-known to a person skilled in the art, including the specific embodiments listed below, the embodiments by a combination with other chemical synthesis processes, and equivalent alternatives well known to a person skilled in the art. The preferable embodiments include but are not limited to the Examples below.

The chemical reaction of the specific embodiments is performed in a suitable solvent, and the solvent should be suitable for the chemical changes of the present disclosure and the required reagents and materials. To obtain the compound of the present disclosure, a person skilled in the art can modify or select a synthesis step or a reaction scheme based on the available embodiments.

The present disclosure will be described in a detailed manner and the Examples should be not considered as limitation thereto.

The solvents used herein are commercially available and can be used without further purification.

The solvents used herein can be commercially available. The following abbreviations are used herein: DCM represents dichloromethane; DMF represents N,N-dimethyl sulfoxide dimethylformamide; DMSO represents dimethyl sulfoxide; EtOH represents ethanol; MeOH represents methanol; TFA represents trifluoroacetic acid; TsOH represents p-toluenesulfonic acid; mp represents melting point; EtSO$_3$H represents ethanesulfonic acid; MeSO$_3$H represents methanesulfonic acid; ATP represents adenosine triphosphate; HEPES represents 4-hydroxyethylpiperazine ethanesulfonic acid; EGTA represents ethylenebis(oxyethylenenitrilo)tetraacetic acid; MgCl$_2$ represents magnesium dichloride; MnCl$_2$ represents manganese dichloride; DTT represents dithiothreitol; DCC represents dicyclohexylcarbodiimide; DMAP represents 4-dimethylaminopyridine; DIEA represents N,N-diisopropylethylamine; wt %: mass percentage; THF represents tetrahydrofuran.

Instruments and Analysis Methods 1.1 X-Ray Powder Diffractometer (XRPD)
  Device: BRUKER D8 advance X-Ray diffractometer
  Testing method: about 10-20 mg of sample is used for XRPD detection.
  Detailed XRPD parameters are as follows:
  Light tube: Cu, kα, (λ=1.54056Å).
  Light tube voltage: 40 kV, Light tube current: 40 mA
  Divergence slit: 0.60 mm
  Detector slit: 10.50 mm
  Anti-scatter slit: 7.10 mm
  Scanning range: 4-40 deg
  Step size: 0.02 deg
  Time/step: 0.12 s
  Sample stage spinning speed: 15 rpm 1.2 Differential Scanning Calorimeter (DSC)
  Device: TA Q2000 Differential Scanning calorimeter
  Testing method: The sample (about 1 mg) is placed in DSC aluminum pot for testing, under 50 mL/min N$_2$, is heated from 30° C. to 300° C. at the heating rate of 10° C./min.

1.3 Thermal Gravimetric Analyzer (TGA)
  Device: TA Q5000 Thermal Gravimetric Analyzer
  Testing method: The sample (2-5 mg) is placed in TGA platinum pot for testing, under 25 mL/min N$_2$, is heated at the heating rate of 10° C./min from 30° C. (room temperature) to 300° C., or until weight loss of 20%.

DETAILED DESCRIPTION

Figure 1:
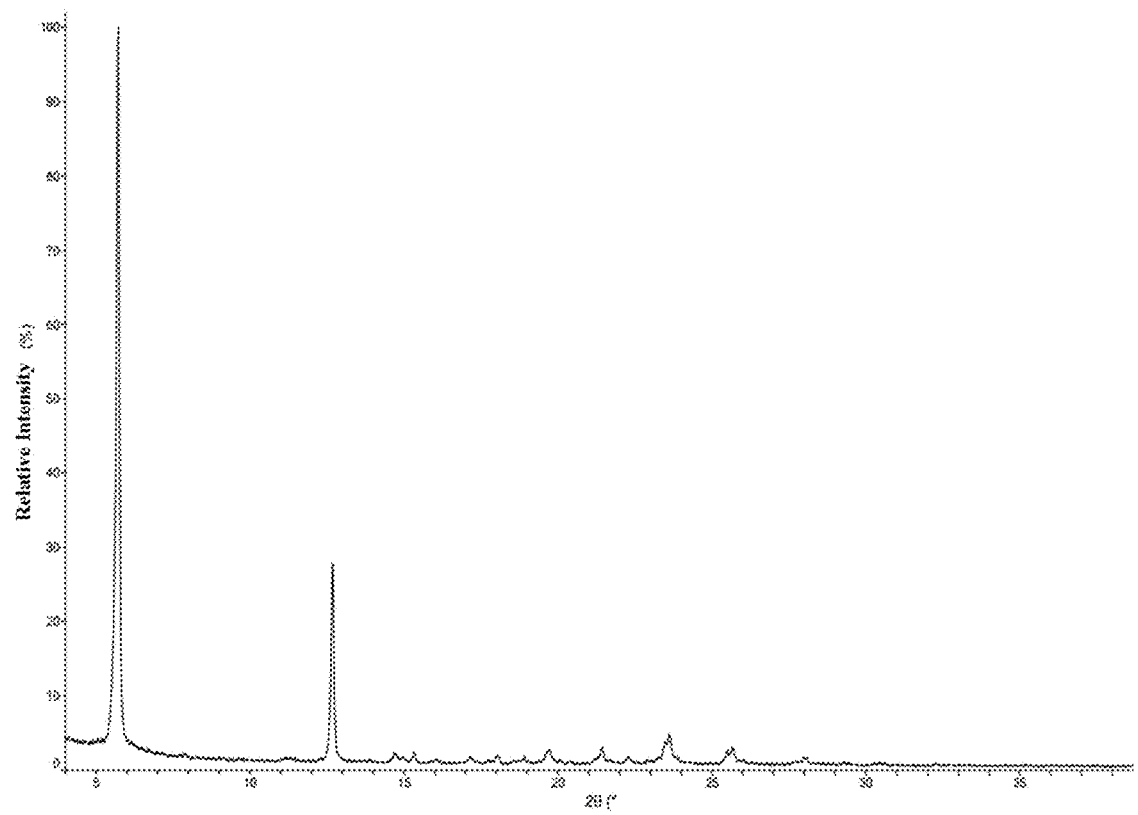
FIG. 1 shows the XRPD pattern at Cu-Kα radiation of the Crystal Form A of the compound of Formula (I)
Figure 2:
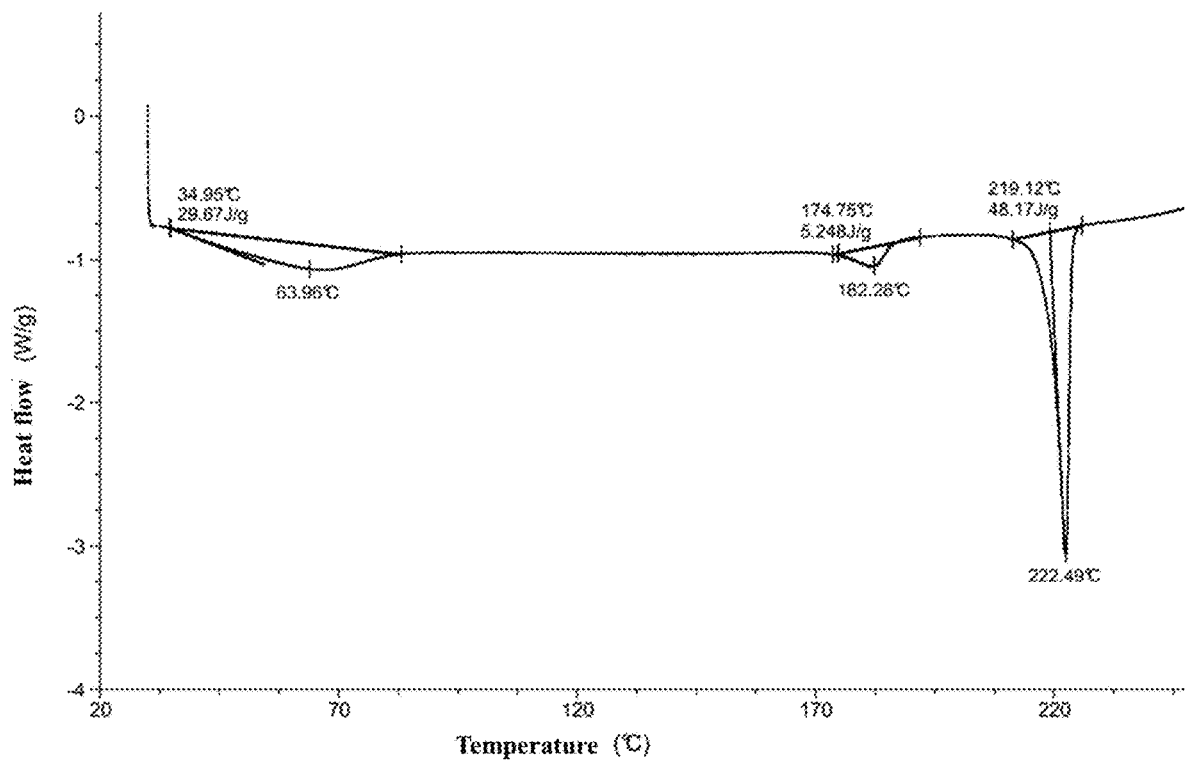
FIG. 2 shows the DSC pattern of the Crystal Form A of the compound of Formula (I)
Figure 3:
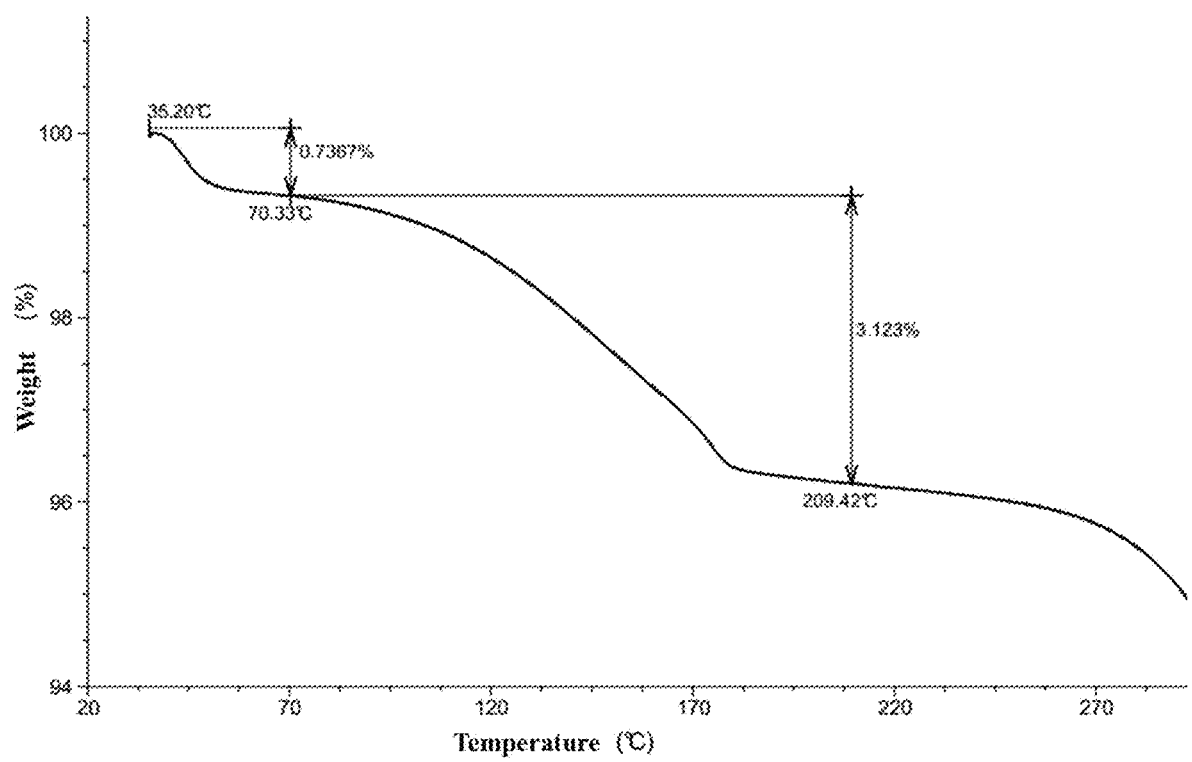
FIG. 3 shows the TGA pattern of the Crystal Form A of the compound of Formula (I)

The present disclosure will be described in detail below by reference to the Examples, which are not to mean any disadvantageous limitation. The present disclosure has been described in detail herein, and its specific embodiments are also disclosed. It will be obvious to those skilled in the art that various changes and improvements can be made to the specific embodiments without departing from the spirit and scope.

Intermediate 1

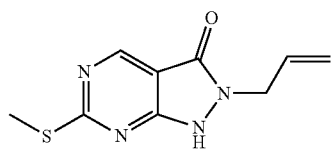

Preparation was performed by reference to the synthesis process in WO2007126122.

Example 1: Compound of Formula (I)

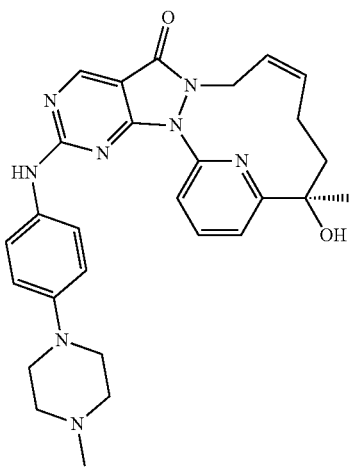

Formula (I)

Synthesis Scheme:

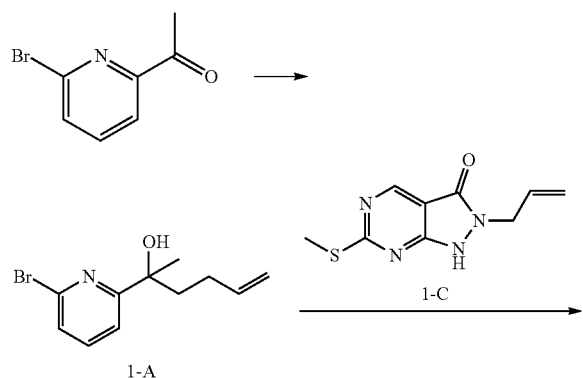

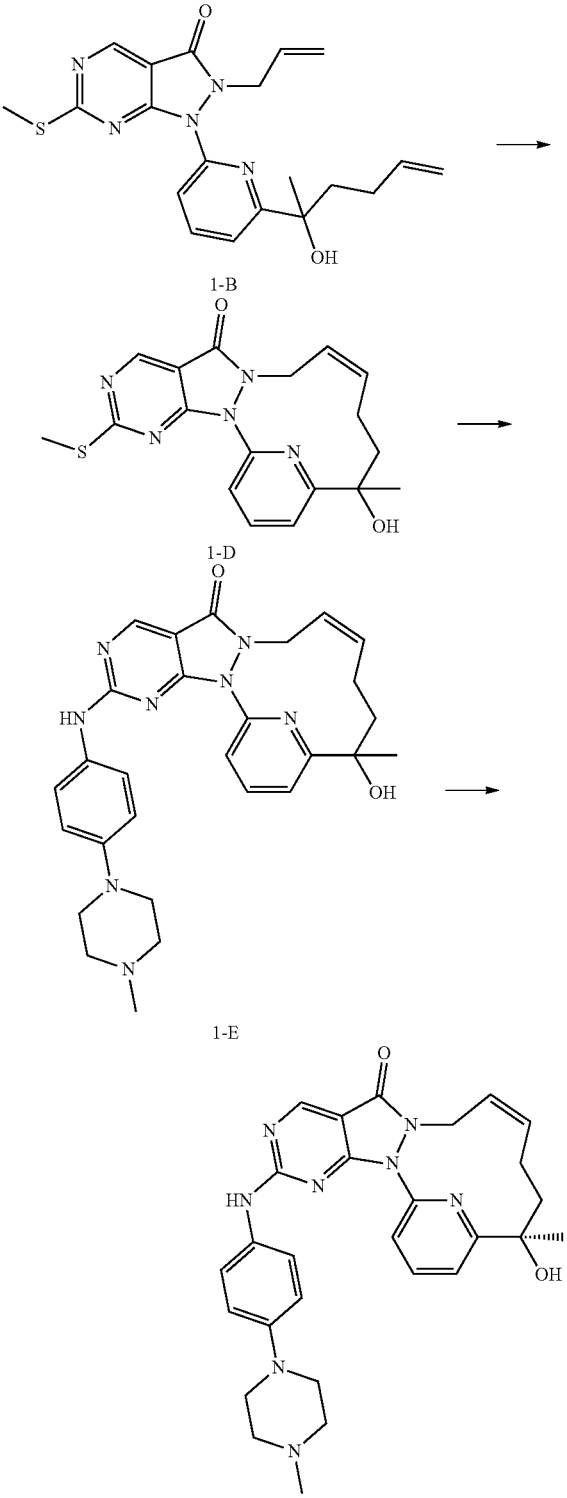

Step 1: Synthesis of Compound 1-A

At 0~15° C. and nitrogen atmosphere, to a solution of 2-acetyl-6-bromopyridine (7.35 g, 36.74 mmol) in THF (150 mL) was added dropwise 3-butenylmagnesium bromide (1 M, 55.12 mL) and then the reaction solution was stirred at 10~20° C. for 3 h. 100 mL of saturated ammonium chloride solution was added to quench the reaction and liquid separation was performed to give an organic layer, which was washed with 50 mL of saturated sodium chloride, dried over anhydrous sodium sulfate, rotated and concentrated to dryness to give a brown oil. The brown oil was purified with silica gel column chromatography (PE/EA=7/1) to give 1-A. $^1$H NMR (400 MHz, DMSO-$d_6$) δ 7.73 (t, J=8.0 Hz, 1H), 7.64 (d, J=7.2 Hz, 1H), 7.46 (d, J=7.2 Hz, 1H), 5.78~5.7 (m, 1H), 4.94~4.85 (m, 2H), 2.07~2.01 (m, 1H), 1.90~1.71 (m, 3H), 1.41 (s, 3H).

Step 2: Synthesis of Compound 1-B

To a mixture of 1-A (3.47 g, 13.55 mmol) and 1-C (3.01 g, 13.55 mmol) in dioxane (150 mL) were added N,N"-dimethylethylenediamine (1.31 g, 14.90 mmol, 1.60 mL), copper iodide (2.58 g, 13.55 mmol) and potassium carbonate (2.62 g, 18.97 mmol), which was purged with nitrogen three times. The mixture was stirred at 95° C. and nitrogen atmosphere for 1.5 and 200 mL of ammonia (28%) was added. The reaction mixture was extracted with ethyl acetate (300 mL×2) and the organic layers were combined, washed with 200 mL of saturated brine, dried over anhydrous sodium sulfate, and concentrated under reduced pressure to dryness. The mixture was purified with silica gel column chromatography (PE/EA=3/1) to give 1-B. $^1$H NMR (400 MHz, DMSO-$d_6$) δ 9.02 (s, 1H), 8.04 (t, J=8.0 Hz, 1H), 7.76 (d, J=7.2 Hz, 1H), 7.64 (d, J=7.6 Hz, 1H), 5.7~75.67 (m, 2H), 5.01~4.79 (m, 6H), 2.56 (s, 3H), 2.15~2.11 (m, 1H), 1.85~1.75 (m, 2H), 1.70~1.60 (m, 1H), 1.46 (s, 3H).

Step 3: Synthesis of Compound 1-D

To a solution of 1-B (2.06 g, 5.18 mmol) in toluene (700 mL) was added Grubbs second generation catalyst (1.32 g, 1.55 mmol), and the mixture was stirred for 6 h at 80° C. and nitrogen atmosphere. Grubbs second generation catalyst (0.65 g, 0.775 mmol) was further added and the mixture was stirred at 80° C. and nitrogen atmosphere for 3 h. The mixture was cooled to room temperature and filtered. The filtrate was concentrated to dryness to give a brown residue, which was purified with silica gel column chromatography (PE/EA=1/1) to give 1-D. $^1$H NMR (400 MHz, DMSO-$d_6$) δ 9.07 (s, 1H), 8.06 (t, J=8.0 Hz, 1H), 7.79 (d, J=8.2 Hz, 1H), 7.70 (d, J=7.6 Hz, 1H), 5.39~5.25 (m, 3H), 4.66 (d, J=5.2 Hz, 2H), 2.62 (s, 3H), 2.4~01.95 (m, 3H), 1.85~1.65 (m, 1H), 1.64 (s, 3H).

Step 4: Synthesis of Compound 1-E

To a solution of Compound 1-D (360 mg, 974.45 μmol) in toluene (35 mL) was added meta-chloroperbenzoic acid (265.09 mg, 1.31 mmol, 85% purity) and the reaction system was stirred at 25° C. for 2 h. To the reaction solution were added 4-(4-methylpiperazion)aniline (242.30 mg, 1.27 mmol) and N,N-diisopropylethylamine (503.76 mg, 3.90 mmol). The reaction solution was stirred at 25° C. for 12 h. To the reaction solution was added 25 mL of water with stirring and the aqueous phase was extracted with ethyl acetate (30 mL×3). The organic phases were combined, washed once with saturated sodium bicarbonate solution (30 mL) and saturated brine (30 mL), respectively, dried over anhydrous sodium sulfate, filtered and dried under vacuum to give a crude, which was separated with preparative liquid chromatography (neutral) to give 1-E. $^1$H NMR (400 MHz, CDCl$_3$) δ ppm 1.70 (s, 3H) 1.78 (br d, J=13.54 Hz, 2H), 2.04 (br d, J=6.54 Hz, 1H), 2.08-2.23 (m, 2H), 2.39 (s, 3H), 2.62-2.64 (m, 4H), 3.21-3.24 (m, 4H), 4.24 (br s, 1H), 4.51 (br d, J=13.54 Hz, 1H), 5.61-5.88 (m, 2H), 6.95 (d, J=9.04 Hz, 2H) 7.49 (d, J=9.04 Hz, 3H), 7.81-7.90 (m, 2H) 8.87 (s, 1H); MS m/z: 513.1 [M+H]$^+$.

Step 5: Synthesis of Compound of Formula (I)

Compound 1-E (100 mg, 195.08 μmop was subjected to SFC chiral resolution (chromatography column: AD 250×50 mm I.D., 10 μm mobile phase: A: supercritical CO$_2$, B: EtOH (0.1% NH$_3$H$_2$O), A:B=55:45 at 200 mL/min), retention time: 21 min, to give the compound of Formula (I). $^1$H NMR (400 MHz, CDCl$_3$) δ ppm 1.60 (s, 3H), 1.68 (br s, 2H), 1.94 (br d, J=7.04 Hz, 1H), 2.00-2.20 (m, 2H), 2.30 (s, 3H), 2.52-2.55 (m, 4H), 3.12-3.15 (m, 4H), 4.24 (br s, 1H), 4.42 (br d, J=9.54 Hz, 1H), 5.65 (br s, 2H), 6.85 (d, J=9.04 Hz, 2H), 7.17 (s, 1H) 7.40 (d, J=9.04 Hz, 2H), 7.69-7.81 (m, 2H), 8.77 (s, 1H). MS m/z: 513.1 [M+H]$^+$.

Example 2: Preparation of Crystal Form A of the Compound of Formula (I)

About 50 mg of the Compound of Formula (I) was added into various glass bottles, to which were added 0.5 mL of acetone respectively to form a suspension. The suspension samples were tested in a constant temperature shaking apparatus (40° C.). The suspension samples were shaken at 40° C. for 2 days and centrifuged. The upper liquid was removed, and the residual samples were dried in a vacuum drying cabinet (40° C.) overnight to give Crystal Form A of the Compound of Formula (I).

Example 3: Preparation of Crystal Form B of the Compound of Formula (I)

About 50 mg of the Compound of Formula (I) was added into various glass bottles, to which were added 0.3 mL of ethanol respectively to form a suspension. The suspension samples were tested in a constant temperature shaking apparatus (40° C.). The suspension samples were shaken at 40° C. for 2 days and centrifuged. The upper liquid was removed, and the residual samples were dried in a vacuum drying cabinet (40° C.) overnight to give Crystal Form B of the Compound of Formula (I).

Example 4: Preparation of Crystal Form C of the Compound of Formula (I)

About 50 mg of the Compound of Formula (I) was added into various glass bottles, to which were added 0.2 mL of methanol respectively to form a suspension. The suspension samples were tested in a constant temperature shaking apparatus (40° C.). The suspension samples were shaken at 40° C. for 2 days and centrifuged. The upper liquid was removed, and the residual samples were dried in a vacuum drying cabinet (40° C.) overnight to give Crystal Form C of the Compound of Formula (I).

Example 5: Preparation of Crystal Form D of the Compound of Formula (I)

About 50 mg of the Compound of Formula (I) was added into various glass bottles, to which were added 0.4 mL of methanol/water (1/1) respectively to form a suspension. The suspension samples were tested in a constant temperature shaking apparatus (40° C.). The suspension samples were shaken at 40° C. for 2 days and centrifuged. The upper liquid was removed, and the residual samples were dried in a vacuum drying cabinet (40° C.) overnight to give Crystal Form D of the Compound of Formula (I).

Example 6: Preparation of Crystal Form E of the Compound of Formula (I)

About 50 mg of the Compound of Formula (I) was added into various glass bottles, to which were added 0.5 mL of acetonitrile respectively to form a suspension. The suspension samples were tested in a constant temperature shaking apparatus (40° C.). The suspension samples were shaken at 40° C. for 2 days and centrifuged. The upper liquid was removed, and the residual samples were dried in a vacuum drying cabinet (40° C.) overnight to give Crystal Form E of the Compound of Formula (I).

Example 7: Preparation of Crystal Form F of the Compound of Formula (I)

At 25-26° C., to a 1 L three-necked flask with 560 mL of MeOH was added the Compound of Formula (I) with stirring. The reaction system was heated in an oil bath to 55~65° C. After 20 min, the inner temperature was maintained as 47° C.-53° C. and the reaction system was stirred for 72 h at maintained temperature. Heating was stopped and stirring was continued with the temperature was spontaneously lowered for 1 h to 27° C. The system was allowed to stand for 18 h and filtered and the filter cake was rinsed with 30 mL of MeOH. The filter cake was dried at 60° C. under vacuum for 48 h to give Crystal Form F of the Compound of Formula (I).

Experimental Example 1: Solid Stability Test of Crystal Form F of the Compound of Formula (I) Under High Temperature, High Humidity, Illumination Conditions According to influencing factors and accelerated test conditions, about 5 mg of Crystal Form F of the Compound of Formula (I) was weighed precisely and placed in a dry and clean glass bottle, in duplicate, and spread into a thin layer, as the formal test sample, placed under the influencing factors test conditions (60° C., 92.5% RH (relative humidity)) and accelerated conditions (40° C./75% RH and 60° C./75% RH), with the samples fully exposed. The test system was covered with an aluminum foil paper with small holes. In addition, a small amount of samples were taken and placed in a 40 mL glass sample bottle under the same conditions to determine the crystal state. Sampling and analysis were performed on day 5 days, 10 days, and one month. The analysis method was shown in Table 7, and the analysis results were shown in Table 8. The samples placed under Illumination (visible light 1200000 Lux, UV 200 W) conditions were fully exposed at room temperature.

TABLE 7

Analytical method of related substances by high performance liquid chromatography

| Chromatography column | waters xbridge shield RP18(4.6 mm × 150 mm, 3.5 μm), PN: 186003045 |
| --- | --- |
| Wavelength | 230 nm |
| Column temperature | 40° C. |
| Flow rate | 0.8 mL/min |
| Injecting volume | 10 μL |
| Mobile phase | A: 5 mmol/L ammonium acetate solution(pH 4.5)(V/V) B: 100% ACN |

| Mobile phase program | Time (min) | A % | B % |
| --- | --- | --- | --- |
| | 0.01 | 95 | 5 |
| | 10.00 | 95 | 5 |
| | 50.00 | 30 | 70 |
| | 51.00 | 10 | 90 |
| | 55.00 | 10 | 90 |

TABLE 7-continued

Analytical method of related substances by high performance liquid chromatography

| | 56.00 | 95 | 5 |
| --- | --- | --- | --- |
| | 62.00 | 95 | 5 |
| | 62.01 | stop | |

| Time for data acquisition | 62 min |
| --- | --- |
| Solvent | acetonitrile: water (V/V) = 50:50 |
| Solvent for needle washing | acetonitrile: water (V/V) = 50:50 |

TABLE 8

Analysis results of solid stability sample content and related substance for Crystal Form F of the Compound of Formula (I) (5 days, 10 days, one month)

| Conditions and time points | Crystal Form | Total impurity % | Content % |
| --- | --- | --- | --- |
| 0 day | Crystal Form F | 0.63 | 99.38 |
| 60° C._5 days | Crystal Form F | 0.74 | 99.39 |
| 60° C._10 days | Crystal Form F | 0.84 | 99.98 |
| 92.5% humidity_5 days | Crystal Form F | 0.61 | 98.72 |
| 92.5% humidity_10 days | Crystal Form F | 0.64 | 98.38 |
| Protection from light | Crystal Form F | 0.61 | 97.77 |
| Illumination | Crystal Form F | 0.67 | 98.58 |
| 40° C. -75% humidity-10 day | Crystal Form F | 0.63 | 98.01 |
| 40° C. -75% humidity-1 month | Crystal Form F | 0.62 | 97.94 |
| 60° C. -75% humidity-10 day | Crystal Form F | 0.69 | 100.43 |
| 60° C. -75% humidity-1 month | Crystal Form F | 0.75 | 99.46 |

Conclusion: Crystal Form F of the Compound of Formula (I) did not change for raw material compound crystal form during the one-month solid influencing factor and accelerated test, showing good physical stability. In the analysis of related substances, the impurities were slightly increased at high temperature (60° C.) and accelerated conditions (60° C./75% RH), and the total amount of impurities was almost unchanged under other conditions, showing slight sensitivity to temperature.

Experimental conclusion: The crystal form of the present disclosure has good stability and is easy for medicine manufacture.

Experimental Example 2: In Vitro Enzymatic Inhibitory Activity of the Compound of Formula (I)

The experimental test was carried out in Eurofins, and the experimental results were provided by the company.

Into the test system were added 20 mM Tris-HCl, pH 8.5, 0.2 mM EDTA, 500 μM polypeptide substrate (LSN-LYHQGKFLQTFCGSPLYRRR), 10 mM magnesium acetate and 10 μM [γ-$^{33}$P]-ATP (intensity of about 500 cpm/pmol). After addition of $Mg^{2+}$ and ATP mixture, the reaction was initiated and incubated at room temperature for 40 min. 3% phosphate buffer was added to stop the reaction.

10 μL of reaction solution was taken and filtered on a continuous filter P30, and washed three times with 75 mM phosphate buffer, once with methanol, each washing for 5 min. After drying, the values were read by scintillation counting method. The test results were shown in Table 9.

TABLE 9

In vitro enzymatic activity test results of the compounds of the present disclosure (IC$_{50}$)

| Compound No. | Wee1 (IC$_{50}$ nM) |
|---|---|
| AZD1775 | 47 |
| Compound of Formula (I) | 29 |

Experimental Example 3: In Vitro Permeability Test of the Compound of the Present Disclosure MDR1-MDCK II cell authorized by the Piet Borst Laboratory of the Netherlands Cancer Institute was used in the study, the cell is a Madin-Darby canine kidney cell transfected with the human multi-drug resistance gene (MDR1), which can stably express efflux transporter P glycoprotein (P-gp) and therefore is suitable for screening P-gp substrate or inhibitor, and for predicting the permeability of compounds with high efflux barriers such as duodenum, blood-brain barrier, liver cell nucleus, and kidney unit. MDR1-MDCK II cells of from passage 5-35 were used for permeability study.

MDR1-MDCK II cells were cultured with α-MEM medium (α-Minimum Essential Media) under culture condition of 37±1° C., 5% CO$_2$ and saturated relative humidity. Then, the cells were seeded in a BD Transwell-96 well plate at a seeding density of 2.3×10$^5$ cells/cm$^2$, and then the cells were cultured in a carbon dioxide incubator for 4-7 days for transport experiment. The preparation method of its α-MEM medium was as follows:

The liquid nutrient base was prepared with powder (α-MEM powder from Gibco, Cat #:11900) dissolved in pure water, and was added with L- (L-glutamine) and NaHCO$_3$. Then 10% FBS (fetal bovine serum), 1% PS (double antibody) and 1% NEAA were added upon use to make a complete medium. The α-MEM medium batch was shown in Table 10.

TABLE 10

αMEM (1 L×) batch table
αMEM (1 L×) batch table

| Compound (1 L×) | Molecular weight. | Concentration (mM) | Amount (mg/L) |
|---|---|---|---|
| Medium powder | / | / | 1 pack |
| L-glutamine | 146 | 2 | 292 |
| NaHCO$_3$ | 84 | 17.85 | 1500 |

AZD1775 (or the compound of the present disclosure) and Digoxin were administered at a concentration of 2 μM, two-way (A-B and B-A directions), with duplicate wells. The test concentrations of Fenoterol and Propranolol were both 2 μM and were administered in one direction (A-B direction), with duplicate wells.

The solutions to be used were pre-incubated in a 37±1° C. water bath for 30 min. The dosing solution and the receiving solution were added to the corresponding cell plate wells (75 and 250 μL for each top and base well, respectively) respectively to initiate the two-way transport experiment. After addition of the samples, the cell plates were placed in an incubator at 37±1° C., 5% CO$_2$ and saturated relative humidity to be incubated for 150 min. The sample collection information was listed in Table 11.

TABLE 11

The sample collection information

| Sample Type | Sample volume per well (μL) | Volume of stop solution (μL) | Volume of transport buffer (μL) |
|---|---|---|---|
| A-B Dosing end | 50 | 250 | 100 |
| A-B Receiving end | 150 | 250 | 0 |
| B-A Dosing end | 50 | 250 | 100 |
| B-A Receiving end | 50 | 250 | 100 |
| T$_0$ | 50 | 250 | 100 |

Note:
T$_0$ refers to a sample of the initial dosing solution.

After all samples were vortexed and centrifuged at 3220 g for 10 min, an appropriate volume of supernatant was transferred to the sample analysis plate. After the plate was sealed, the sample should be stored at 2-8° C. if it was not analyzed immediately, using the LC-MS/MS method for analysis.

After the transport experiment was over, the integrity of the MDR1-MDCK II cells was tested by the Lucifer Yellow Rejection Assay. After 30 min of incubation with the Lucifer Yellow solution, the Lucifer Yellow sample was collected, and the 2e plate reader set at 425/528 nm (Excitation/Emission) was used to detect the relative fluorescence intensity (RFU) of fluorescent yellow in the sample.

Semi-quantitative analysis of the test substance AZD1775 (or the compound of the present disclosure) was performed, where the reference substance Fenoterol, Propranolol and Digoxin, the ratio of the peak area of the analyte to that of the internal standard was used as the concentration of the reference substance.

The experimental results were shown in Table 12.

TABLE 12

Penetration rate (10$^{-6}$ cm/s)

| | AZD1775 | Compound of Formula (I) |
|---|---|---|
| A to B | 2.83 | 4.55 |
| B to A | 29.3 | 17.38 |
| Efflux ratio | 10.37 | 3.82 |

Experimental Conclusion:
Compared with AZD1775, the permeability property of the compound of Formula (I) was greatly improved, which is beneficial for the utilization of drugs by organisms.

Experimental Example 4: Compound Pharmacokinetic Evaluation

This experiment is used to study the pharmacokinetics of AZD1775 (or the compound of the present disclosure) in the plasma of female Balb/c Nude mice after a single intravenous administration and a single oral administration.

Twelve mice (provided by Lingchang) were randomly divided into two groups, 6 females in each group, and samples were collected by cross-blood sampling. All animals in the intravenous group were given 1 mg/kg of AZD1775 (or the compound of the present disclosure) by intravenous injection, and the vehicle formulation was a clear solution of 5% HP-betaCD (Kunshan Ruisk Chemical Materials Co., Ltd.) containing 0.2 mg/mL AZD1775 (or the compound of the present disclosure). The animals in the oral group were given 10 mg/kg of AZD1775 (or the compound of the present disclosures) by gavage, and the vehicle formulation was an uniform suspension of 0.5% methylcellulose containing 1 mg/mL AZD1775 (or the compound of the present disclosure).

In the intravenous group, plasma samples were collected at 9 time points: 5 min, 15 min, 30 min, 1 h, 2 h, 4 h, 6 h, 8 h, and 24 h after the administration. In the oral group, plasma samples were collected at 8 time points: 15 min, 30 min, 1 h, 2 h, 4 h, 6 h, 8 h and 24 h after the administration. The samples were analyzed by LC-MS/MS to obtain plasma concentration data of AZD1775 (or the compound of the present disclosure), and to calculate the pharmacokinetic parameters, such as peak concentration, peak time, clearance rate, half-life, area under the drug-time curve, bioavailability, etc.

The experimental results were shown in Table 13.

TABLE 13

Pharmacokinetic test results

| Administration Mode/Dose | Intravenous administration, | Administration by gavage, 10 mg/kg | |
|---|---|---|---|
| Test product | 1 mg/kg | Area under the | |
| (compounds prepared in each Example) | Clearance rate (mL/min/kg) | Half-life $T_{1/2}$ (h) | drug-time curve $AUC_{0\text{-}last}$ (nM · hr) | Bioavailability F (%) |
| AZD1775 | 85.7 | 0.252 | 1200 | 31 |
| Compound of Formula (I) | 33.5 | 1.69 | 6037 | 62.4 |

Experimental conclusions: Compared with AZD1775, the compound of Formula (I) can significantly improve multiple indicators of pharmacokinetics in mice, where the in vivo clearance rate, half-life, in vivo concentration integral and bioavailability showed significant advantages.

Experimental Example 5: In Vivo Study (1) In Vivo Pharmacodynamic Study of the Compound on Human Colon Cancer LoVo Cell Subcutaneous Xenograft Tumor BALB/c Nude Mouse Model Experimental method: The selected experimental animals (provided by Shanghai SIPPR-BK Experimental Animal Co., Ltd.) were BALB/c nude mice, 6-8 weeks, weighing 18-22 g.

Human colon cancer LoVo cells were cultured in monolayer in vitro, and culture conditions were Ham's F-12 medium with 10% fetal bovine serum, 100 U/mL penicillin, 100 μg/mL streptomycin and 2 mM glutamine, 37° C., 5% $CO_2$. Trypsin-EDTA was used for routine digestion and passage, twice a week. When the cell saturation is 80%-90%, the cells were collected, counted, and inoculated. 0.1 mL ($10\times10^6$ cells) of LoVo cells were subcutaneously inoculated on the right back of each nude mouse, and group administration was initiated when the average tumor volume reached 213 mm³. Dosage for gavage administration was 40 mg/kg, twice a day. The experimental index was to investigate whether the tumor growth was inhibited, alleviated or cured. The diameters of the tumors were measured with a vernier caliper twice a week. The calculation formula for the tumor volume was $V=0.5a\times b^2$, where a and b represent the long diameter and short diameter of the tumor, respectively.

The anti-tumor efficacy of the compound was evaluated by TGI (%) or the relative tumor growth rate T/C (%). TGI (%) reflects the tumor growth inhibition rate. Calculation of TGI (%): TGI (%)=[(1−(Average tumor volume at the end of administration of a certain treatment group−Average tumor volume at the beginning of administration of the treatment group))/(Average tumor volume at the end of treatment in the solvent control group−Average tumor volume at the beginning of treatment in the solvent control group)]×100%.

The final results of 16 days of administration were shown in Table 14.

TABLE 14

Results of pharmacodynamic test of human colon cancer LoVo cell xenograft tumor mouse model

| Compound | TGI (%) |
|---|---|
| AZD1775 | 26.73 |
| Compound of Formula (I) | 84.74 |

Conclusion: Compared with AZD1775, the compound of the present disclosure can significantly improve the inhibitory effect on mouse body tumors, and the chirality of the compound has an unexpected effect on the in vivo efficacy.

(2) In Vivo Pharmacodynamic Study of the Compound on Human Pancreatic Cancer BxPC-3 BALB/c Nude Mice Subcutaneously Transplanted Tumor Model Experimental procedure: The selected experimental animals were BALB/c nude mice, 6-8 weeks, weighing 18-22 g.

The $10^{th}$ generation of BxPC-3 cells were cultured in monolayer in vitro, and the culture conditions were RPMI 1640 medium (Manufacturer: Gibco, Catalog: 22400-089) with 10% fetal bovine serum, 100 U/mL penicillin and 100 μg/mL Streptomycin, 37° C., 5% $CO_2$, 4 passages. The passage method was twice a week with trypsin-EDTA for routine digestion and passage. When the cell saturation reached 80%-90%, the cells were digested with trypsin-EDTA, counted, and resuspended in PBS at a density of $5\times10^7$ cells/mL. Each animal was inoculated with 0.1 mL ($5\times10^6$ cells) of BxPC-3 cells on the right back. When the average tumor volume reached 153 mm³, they were randomly grouped according to the tumor volume and administration was started. Gavage dosage: 25 mg/Kg, once a day.

The experimental index was to investigate whether the tumor growth was inhibited, alleviated or cured. The diameters of the tumors were measured with a vernier caliper twice a week. The anti-tumor efficacy of the compound was evaluated by TGI (%) or the relative tumor growth rate T/C (%). TGI (%) reflects the tumor growth inhibition rate. Calculation of TGI (%): TGI (%)=[(1−(Average tumor volume at the end of administration of a certain treatment group−Average tumor volume at the beginning of administration of the treatment group))/(Average tumor volume at the end of treatment in the solvent control group−Average tumor volume at the beginning of treatment in the solvent control group)]×100%.

The final experimental results of 27 days of administration for were shown in Table 15.

TABLE 15

Results of pharmacodynamic test in human pancreatic cancer BxPC-3 cell xenograft tumor mouse model

| Compound | TGI (%) |
|---|---|
| AZD1775 | 24.3 |
| Compound of Formula (I) | 73.3 |

Conclusion: It can be seen from Table 15, compared with AZD1775, the compound of Formula (I) can significantly improve the inhibitory effect on mouse body tumors.

(3) In Vivo Anti-Tumor Efficacy of the Compound on CT26 Mouse Colon Cancer Cell Transplanted Tumor Model Experimental procedure: The selected experimental animals were BALB/c nude mice, 7 weeks, weighing 16-20 g, female.

Cells: Mouse colon cancer CT26 cells (Cell Bank of Type Culture Collection Committee of Chinese Academy of Sciences) were cultured in monolayer in vitro, and culture condition was RPMI-1640 medium containing 10% fetal bovine serum, in 37° C., 5% $CO_2$ incubator. Trypsin-EDTA was used for routine digestion and passage. When the cells were in the exponential growth phase and the saturation was 80%-90%, the cells were collected, counted, and inoculated. 0.1 mL of DPBS (containing $3×10^5$ CT26 cells) was subcutaneously inoculated on the right back of each mouse. When the average tumor volume reached 50-70 $mm^3$, randomized administration was carried out according to the tumor volume. Gavage dosage: 30 mg/kg, twice a day.

The experimental index was to investigate whether the tumor growth was inhibited, alleviated or cured. The diameters of the tumors were measured with a vernier caliper twice a week. The anti-tumor efficacy of the compound was evaluated by TGI (%) or the relative tumor growth rate T/C (%). TGI (%) reflects the tumor growth inhibition rate. Calculation of TGI (%): TGI (%)=[(1−(Average tumor volume at the end of administration of a certain treatment group−Average tumor volume at the beginning of administration of the treatment group))/(Average tumor volume at the end of treatment in the solvent control group−Average tumor volume at the beginning of treatment in the solvent control group)]×100%.

The final results of 18 days of administration were shown in Table 16.

TABLE 16

In vivo efficacy test results of mouse colon cancer CT26 cell allograft tumor model

| Compound | TGI (%) |
|---|---|
| AZD1775 | 66.43 |
| Compound of Formula (I) | 93.38 |

Conclusion: It can be seen from Table 16, compared with AZD1775, the compound of Formula (I) can significantly improve the inhibitory effect on mouse body tumors.

The invention claimed is:
1. A crystal form of a compound of Formula (I):

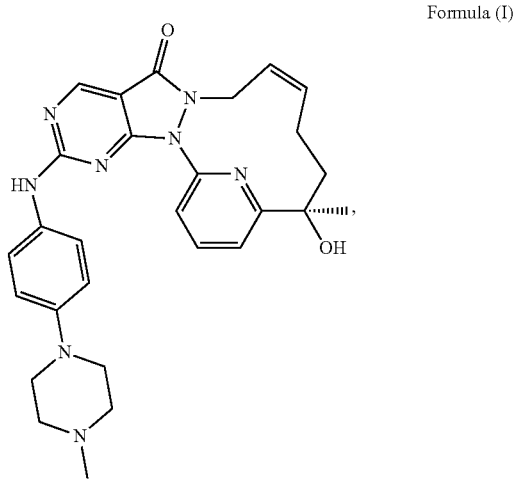 [SMILES: CN1CCN(c2ccc(Nc3ncc4c(=O)n5n(c4n3)-c3cccc(n3)[C@](C)(O)CC/C=C\C5)cc2)CC1]

Formula (I)

selected from the group consisting of:
(1) Crystal Form A, wherein the Crystal Form A has an X-ray powder diffraction (XRPD) pattern having characteristic diffraction peaks at the following 2θ angles: 5.71±0.2°, 12.68±0.2° and 15.32±0.2° at Cu kα radiation with a wavelength of 1.54056 Å;
(2) Crystal Form B, wherein the Crystal Form B has an X-ray powder diffraction (XRPD) pattern having characteristic diffraction peaks at the following 2θ angles: 5.58±0.2°, 12.44±0.2° and 22.16±0.2° at Cu kα radiation with wavelength of 1.54056 Å;
(3) Crystal Form C, wherein the Crystal Form C has an X-ray powder diffraction (XRPD) pattern having characteristic diffraction peaks at the following 2θ angles: 5.05±0.2°, 5.58±0.2° and 12.44±0.2° Cu kα radiation with a wavelength of 1.54056 Å;
(4) Crystal Form D, wherein the Crystal Form D has an X-ray powder diffraction (XRPD) pattern having characteristic diffraction peaks at the following 2θ angles: 5.22±0.2°, 15.99±0.2° and 16.57±0.2° at Cu kα radiation with a wavelength of 1.54056 Å;
(5) Crystal Form E, wherein the Crystal Form E has an X-ray powder diffraction (XRPD) pattern having characteristic diffraction peaks at the following 2θ angles: 8.65±0.2°, 14.22±0.2° and 24.58±0.2° at Cu kα radiation with a wavelength of 1.54056 Å; and
(6) Crystal Form F, wherein the Crystal Form F has an X-ray powder diffraction (XRPD) pattern having characteristic diffraction peaks at the following 2θ angles: 5.06±0.2°, 15.91±0.2° and 16.68±0.2° at Cu kα radiation with a wavelength of 1.54056 Å.

2. The crystal form according to claim 1, being the Crystal Form A having an X-ray powder diffraction pattern having characteristic diffraction peaks at the following 2θ angles: 5.71±0.2°, 12.68±0.2°, 15.32±0.2°, 18.04±0.2°, 19.72±0.2°, 21.44±0.2°, 23.61±0.2° and 25.68±0.2° at Cu kα radiation with a wavelength of 1.54056 Å.

3. The crystal form according to claim 1, being the Crystal Form A having an X-ray powder diffraction pattern as shown in FIG. 1.

4. The crystal form according to claim 1, being the Crystal Form A having a Differential Scanning calorimetry curve (DSC) having one onset point of endothermic peak at 34.95±3° C., 174.75±3° C. and 219.12±3° C., respectively.

5. The crystal form according to claim 1, being the Crystal Form A having a Thermogravimetric Analysis curve (TGA), wherein the weight loss at 70.33±3° C. is 0.7367%, and the weight loss at 209.42±3° C. is 3.123%.

6. The crystal form according to claim 1, being the Crystal Form B having an X-ray powder diffraction pattern having characteristic diffraction peaks at the following 2θ angles: 5.58±0.2°, 11.71±0.2°, 12.44±0.2°, 14.48±0.2°, 15.13±0.2°, 18.64±0.2°, 22.16±0.2° and 26.33±0.2° at Cu kα radiation with a wavelength of 1.54056 Å.

Figure 4:
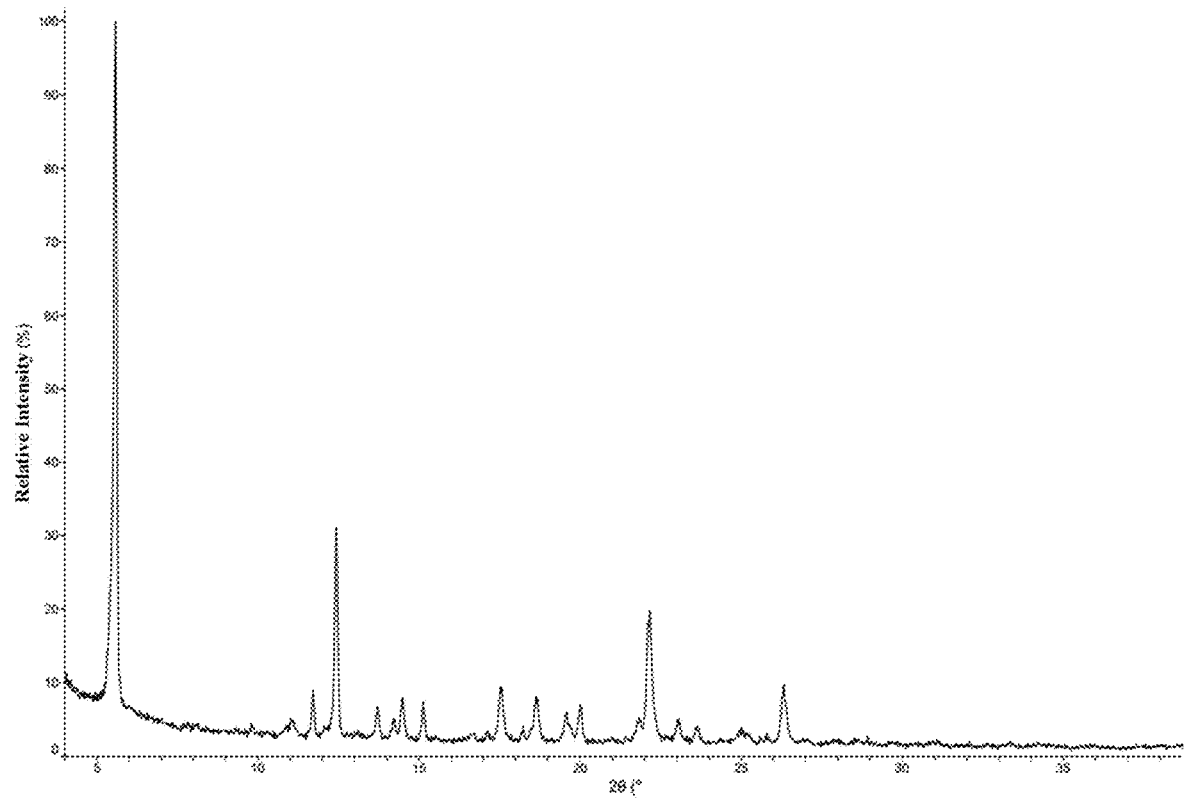
FIG. 4 shows the XRPD pattern at Cu-Kα radiation of the Crystal Form B of the compound of Formula (I)
Figure 5:
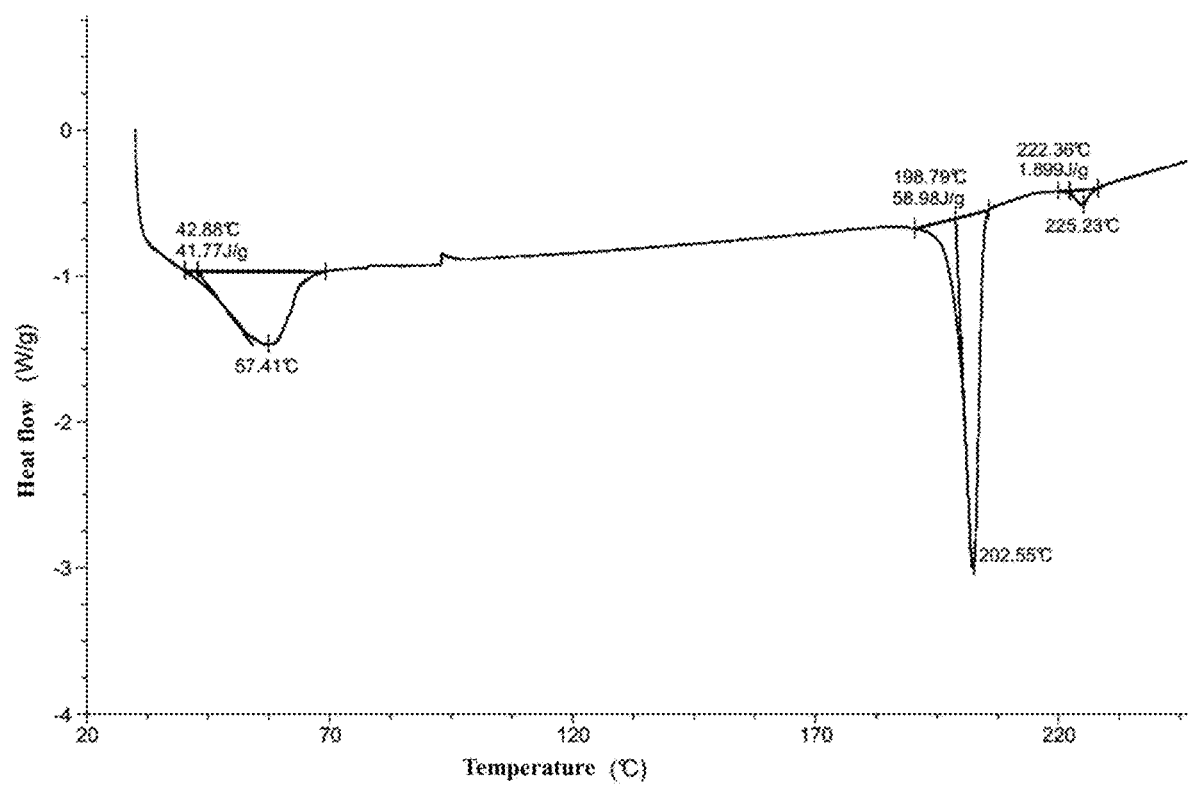
FIG. 5 shows the DSC pattern of the Crystal Form B of the compound of Formula (I)
Figure 6:
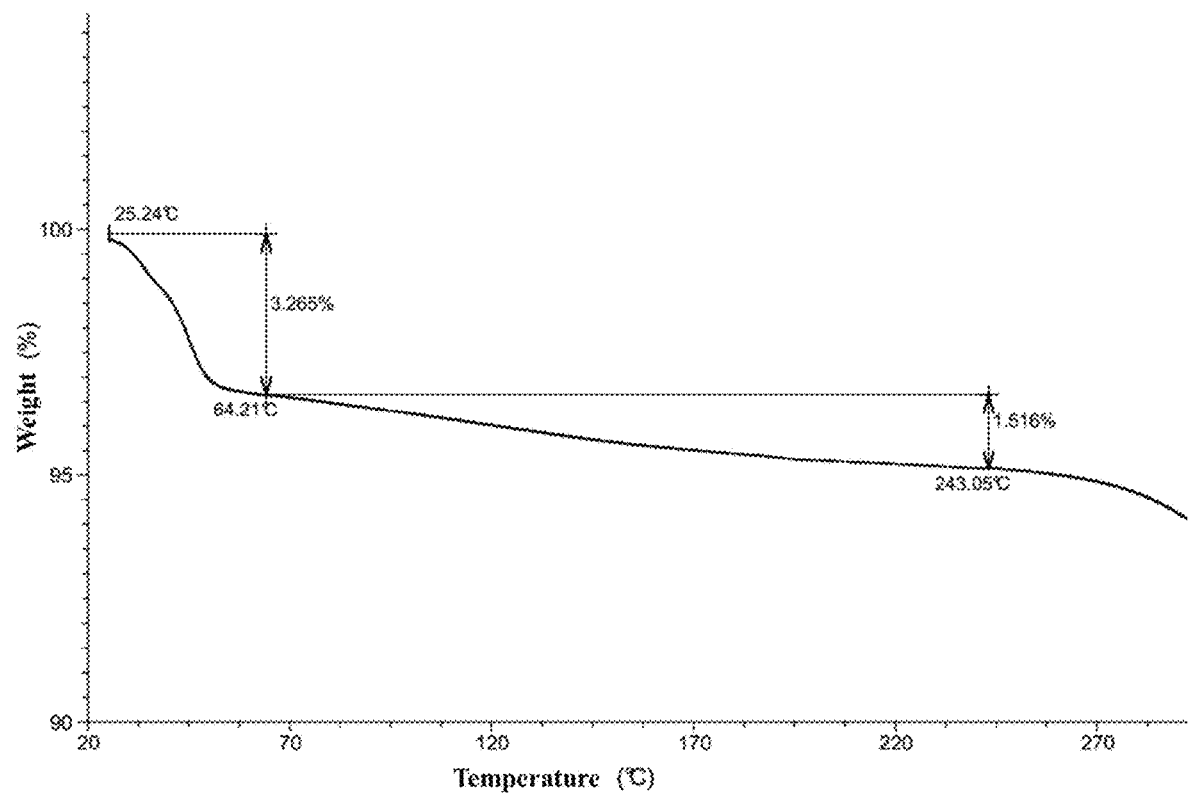
FIG. 6 shows the TGA pattern of the Crystal Form B of the compound of Formula (I)

7. The crystal form according to claim 1, being the Crystal Form B having an XRPD pattern as shown in FIG. 4.

8. The crystal form according to claim 1, being the Crystal Form B having a Differential Scanning calorimetry curve (DSC) having one onset point of endothermic peak at 42.88±3° C., 198.79±3° C. and 222.36±3° C., respectively.

9. The crystal form according to claim 1, being the Crystal Form B having a Thermogravimetric Analysis curve (TGA), wherein the weight loss at 64.21±3° C. is 3.265%; and the weight loss at 243.05±3° C. is 1.516%.

10. The crystal form according to claim 1, being the Crystal Form C having an X-ray powder diffraction pattern having characteristic diffraction peaks at the following 2θ angles: 5.05±0.2°, 5.58=0.2°, 12.44=0.2°, 15.91=0.2°, 16.68=0.2°, 17.61=0.2°, 22.19±0.2° and 26.37±0.2° at Cu kα radiation with a wavelength of 1.54056 Å.

Figure 7:
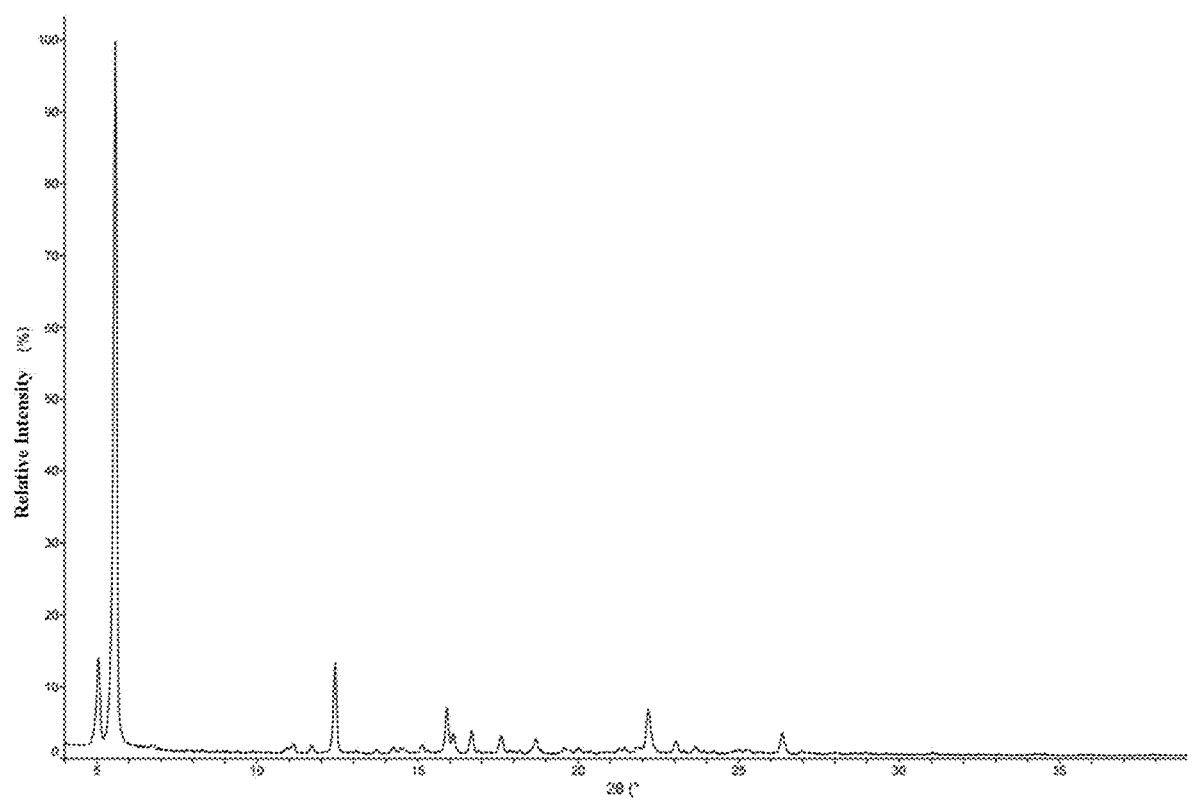
FIG. 7 shows the XRPD pattern at Cu-Kα radiation of the Crystal Form C of the compound of Formula (I)
Figure 8:
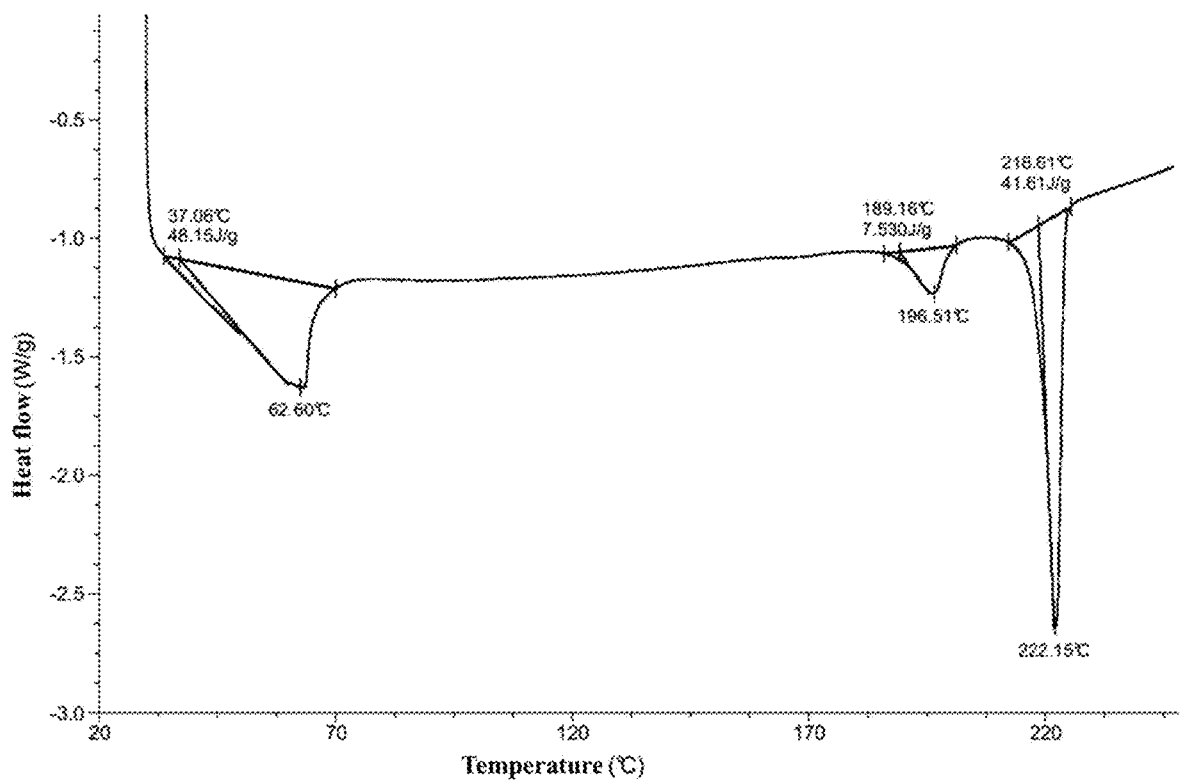
FIG. 8 shows the DSC pattern of the Crystal Form C of the compound of Formula (I)
Figure 9:
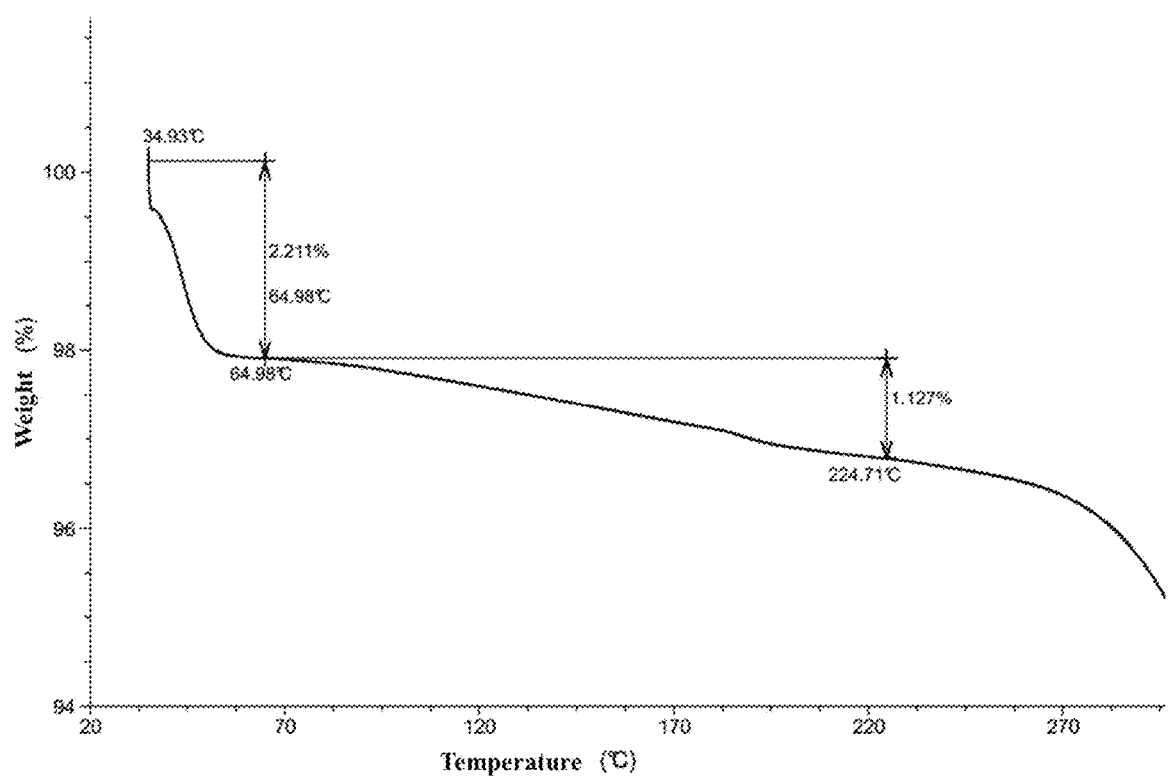
FIG. 9 shows the TGA pattern of the Crystal Form C of the compound of Formula (I)

11. The crystal form according to claim 1, being the Crystal Form C having an XRPD pattern as shown in FIG. 7.

12. The crystal form according to claim 1, being the Crystal Form C having a Differential Scanning calorimetry curve (DSC) having one onset point of endothermic peak at 37.06±3° C., 189.16±3° C. and 218.61±3° C., respectively.

13. The crystal form according to claim 1, being the Crystal Form C having a Thermogravimetric Analysis curve (TGA), wherein the weight loss at 64.98±3° C. is 2.211%; and the weight loss at 224.71±3° C. is 1.127%.

14. The crystal form according to claim 1, being the Crystal Form D having an X-ray powder diffraction pattern having characteristic diffraction peaks at the following 2θ angles: 5.22±0.2°, 15.18±0.2°, 15.99±0.2°, 16.57±0.2°, 17.08±0.2°, 18.60±0.2°, 21.22±0.2° and 21.89±0.2° at Cu kα radiation with a wavelength of 1.54056 Å.

Figure 10:
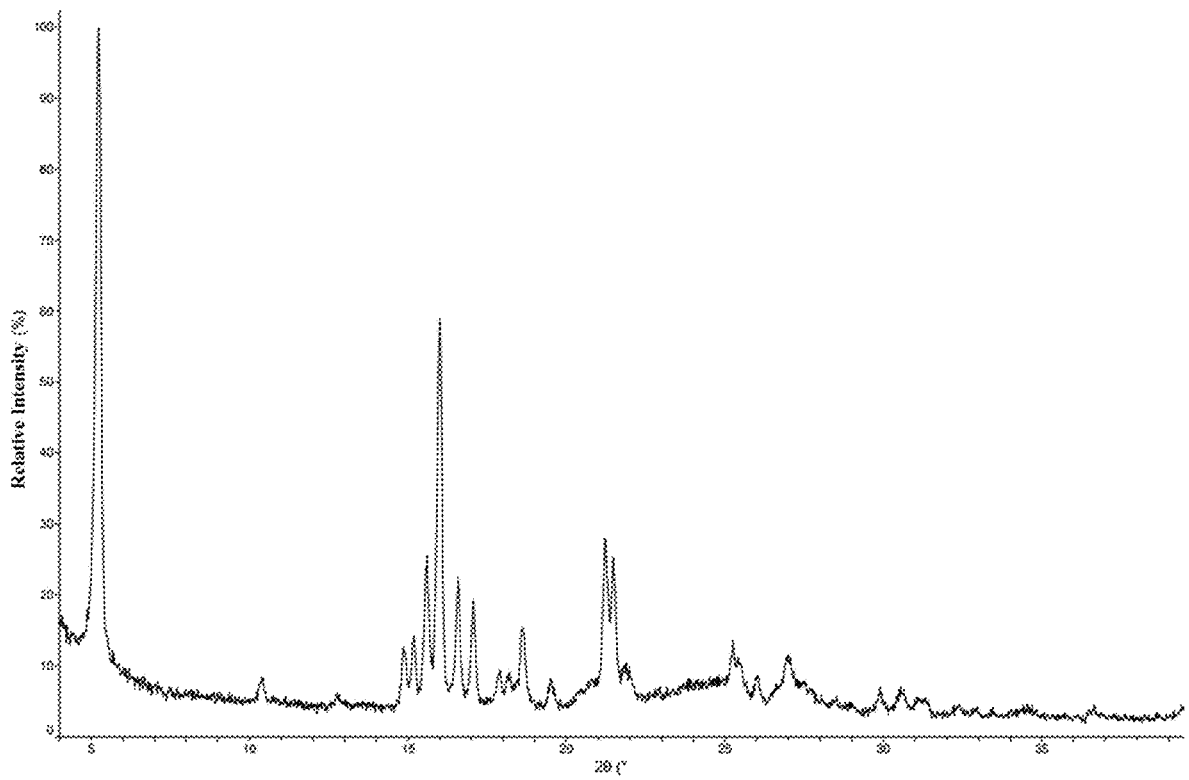
FIG. 10 shows the XRPD pattern at Cu-Kα radiation of the Crystal Form D of the compound of Formula (I)
Figure 11:
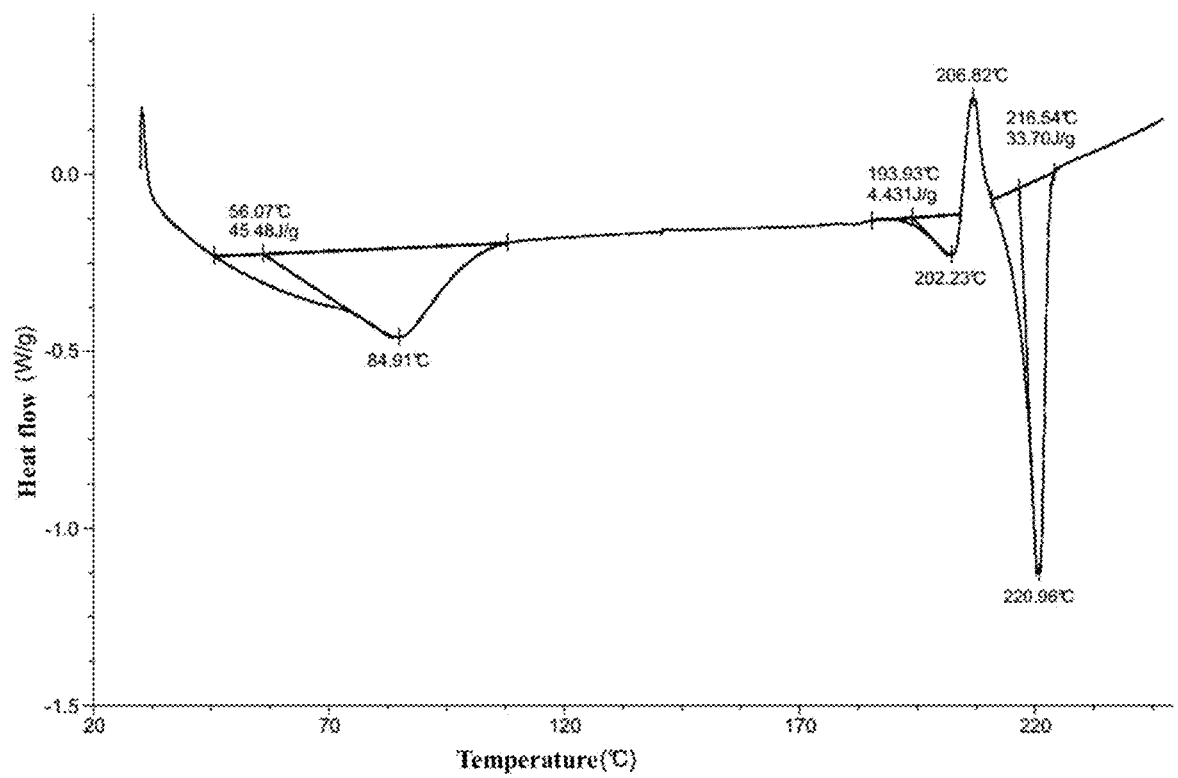
FIG. 11 shows the DSC pattern of the Crystal Form D of the compound of Formula (I)
Figure 12:
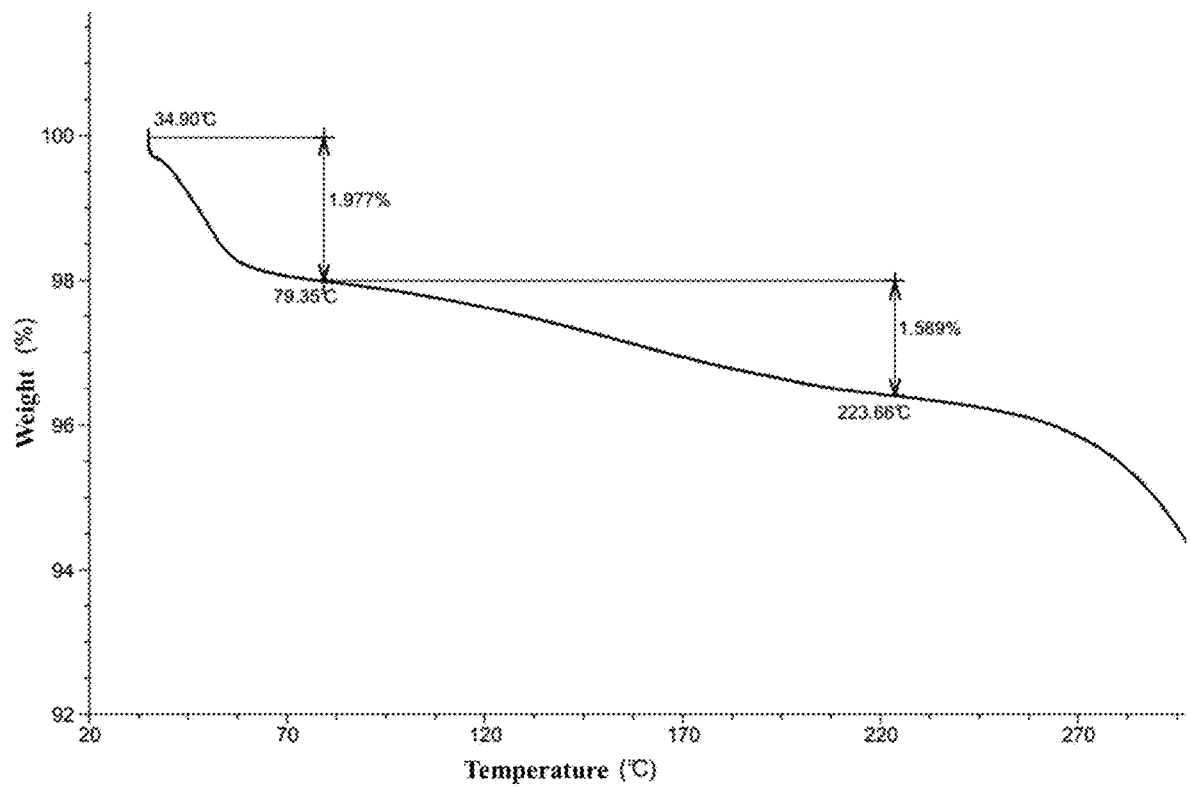
FIG. 12 shows the TGA pattern of the Crystal Form D of the compound of Formula (I)

15. The crystal form according to claim 1, being the Crystal Form D having an XRPD pattern as shown in FIG. 10.

16. The crystal form according to claim 1, being the Crystal Form D having a Differential Scanning calorimetry curve (DSC) having one onset point of endothermic peak at 56.07±3° C., 193.93±3° C. and 216.54±3° C., respectively.

17. The crystal form according to claim 1, being the Crystal Form D having a Thermogravimetric Analysis curve (TGA), wherein the weight loss at 79.35±3° C. is 1.977%; and the weight loss at 223.66±3° C. is 1.589%.

18. The crystal form according to claim 1, being the Crystal Form E having an X-ray powder diffraction pattern having characteristic diffraction peaks at the following 2θ angles: 8.65±0.2°, 11.41±0.2°, 13.13±0.2°, 14.22±0.2°, 17.35±0.2°, 18.34±0.2°, 20.39±0.2°, 20.94±0.2° and 24.58±0.2° at Cu kα radiation with a wavelength of 1.54056 Å.

Figure 13:
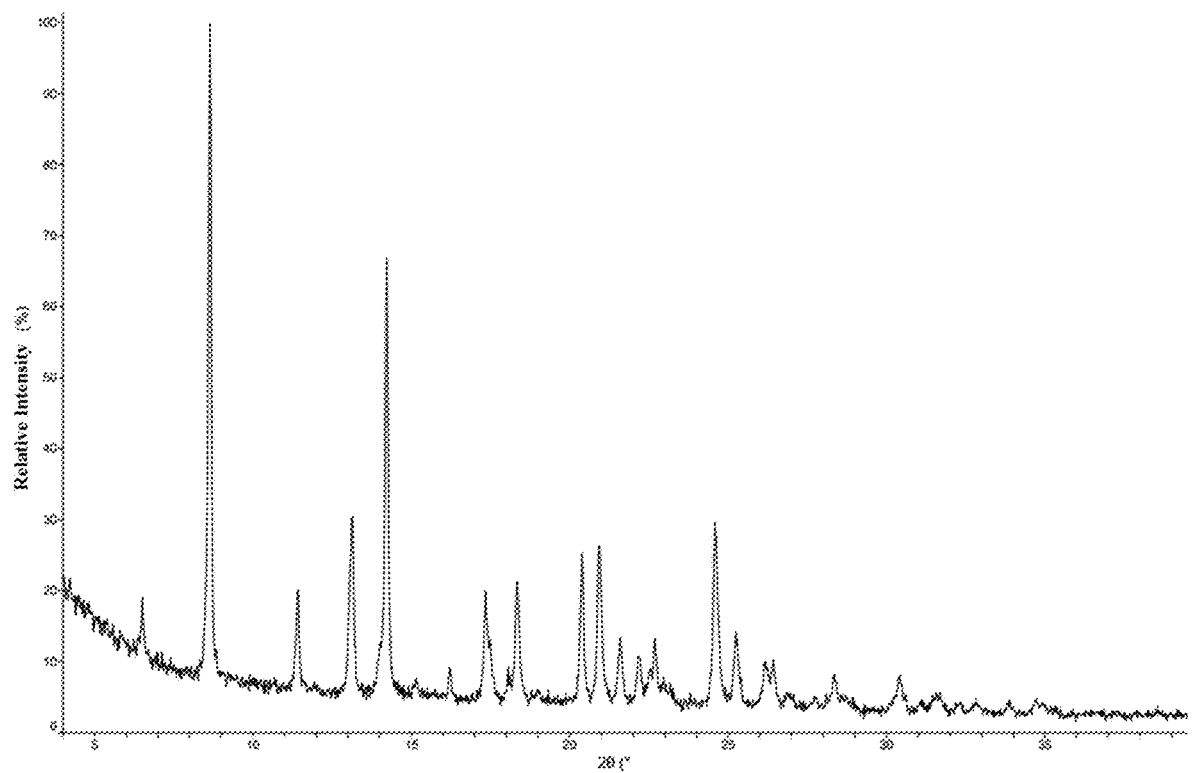
FIG. 13 shows the XRPD pattern at Cu-Kα radiation of the Crystal Form E of the compound of Formula (I)
Figure 14:
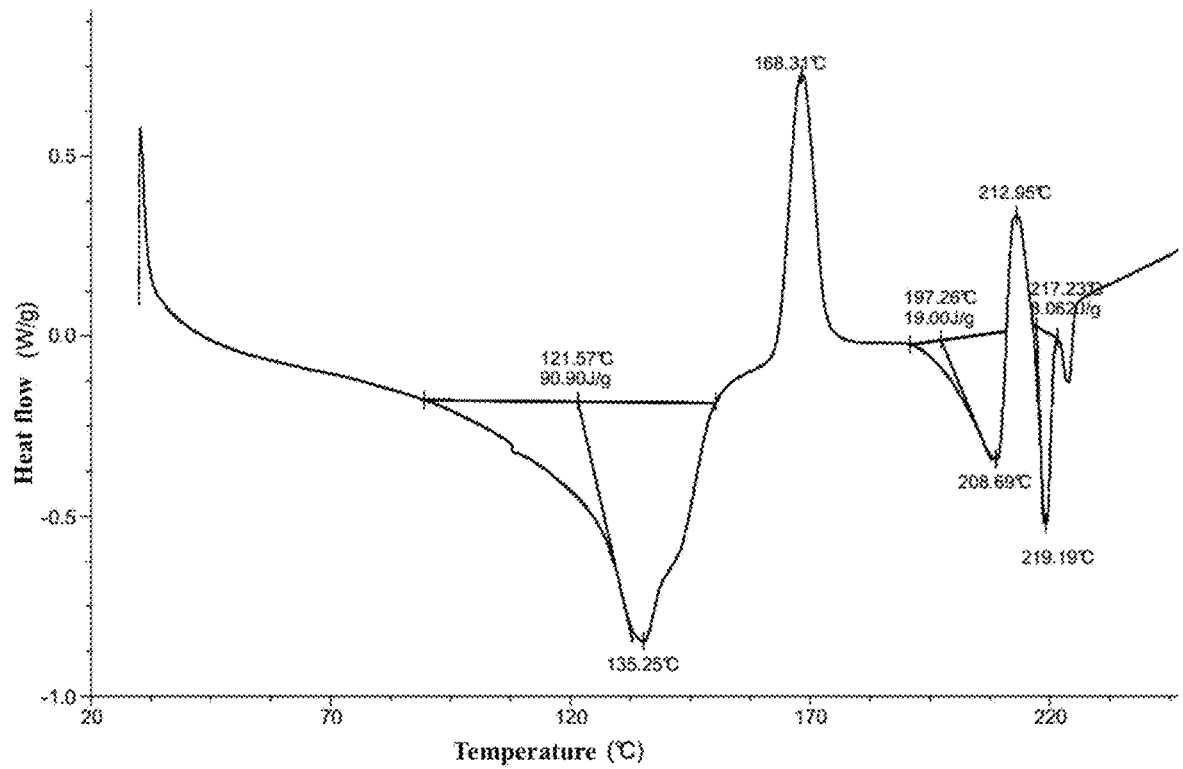
FIG. 14 shows the DSC pattern of the Crystal Form E of the compound of Formula (I)
Figure 15:
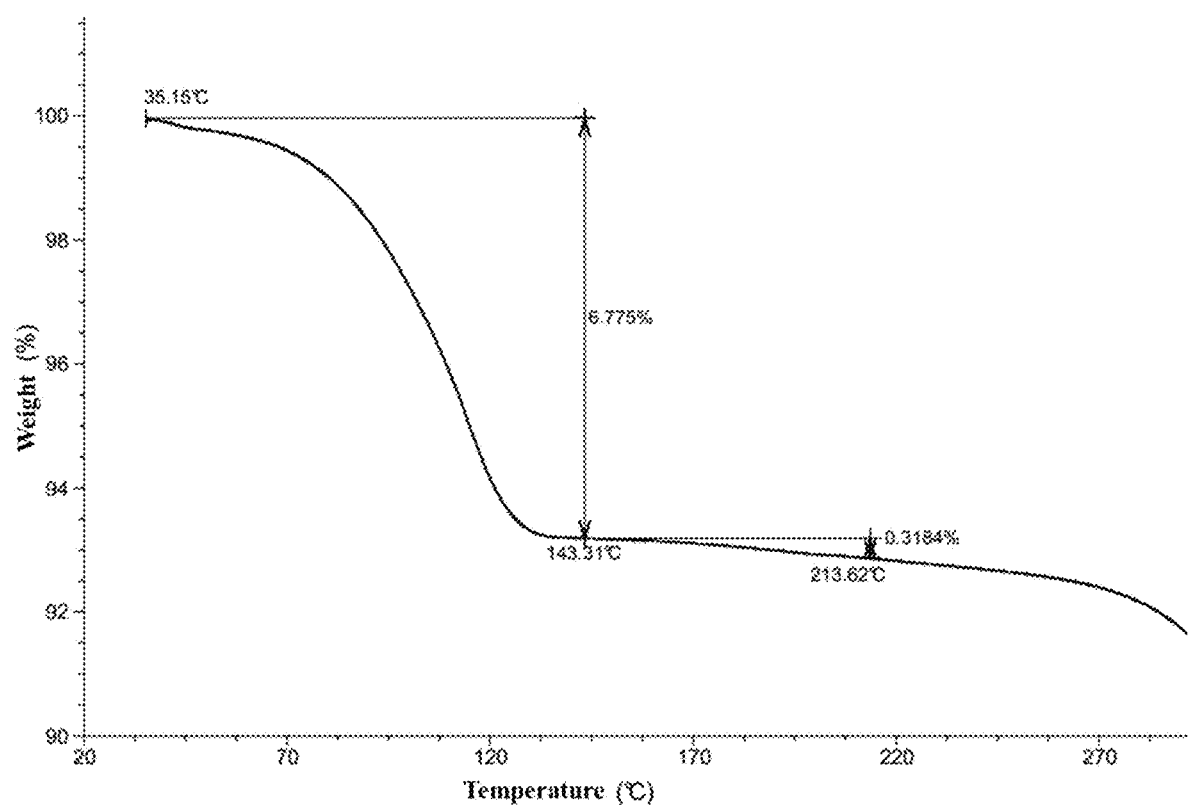
FIG. 15 shows the TGA pattern of the Crystal Form E of the compound of Formula (I)

19. The crystal form according to claim 1, being the Crystal Form E having an XRPD pattern as shown in FIG. 13.

20. The crystal form according to claim 1, being the Crystal Form E having a Differential Scanning calorimetry curve (DSC) having one onset point of endothermic peak at 121.57±3° C., 197.26±3° C. and 217.23±3° C., respectively; and one peak value of exothermic peak at 168.31±3° C. and 212.95±3° C., respectively.

21. The crystal form according to claim 1, being the Crystal Form E having a Thermogravimetric Analysis curve (TGA), wherein the weight loss at 143.31±3° C. is 6.775%; and the weight loss at 213.62±3° C. is 0.3184%.

22. The crystal form according to claim 1, being the Crystal Form F having an X-ray powder diffraction pattern having characteristic diffraction peaks at the following 2θ angles: 5.06±0.2°, 8.34±0.2°, 10.98±0.2°, 15.13=0.2°, 15.91±0.2°, 16.68±0.2°, 17.63=0.2° and 18.87±0.2° at Cu kα radiation with a wavelength of 1.54056 Å.

Figure 16:
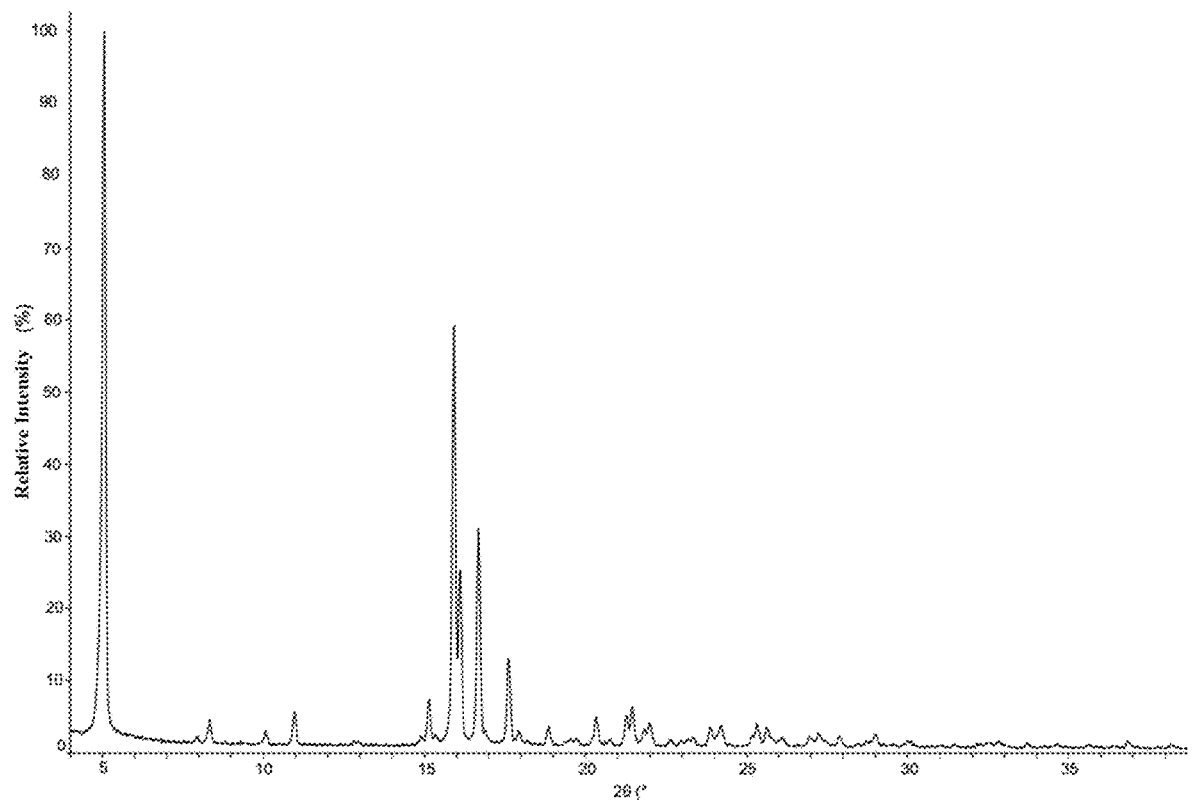
FIG. 16 shows the XRPD pattern at Cu-Kα radiation of the Crystal Form F of the compound of Formula (I)
Figure 17:
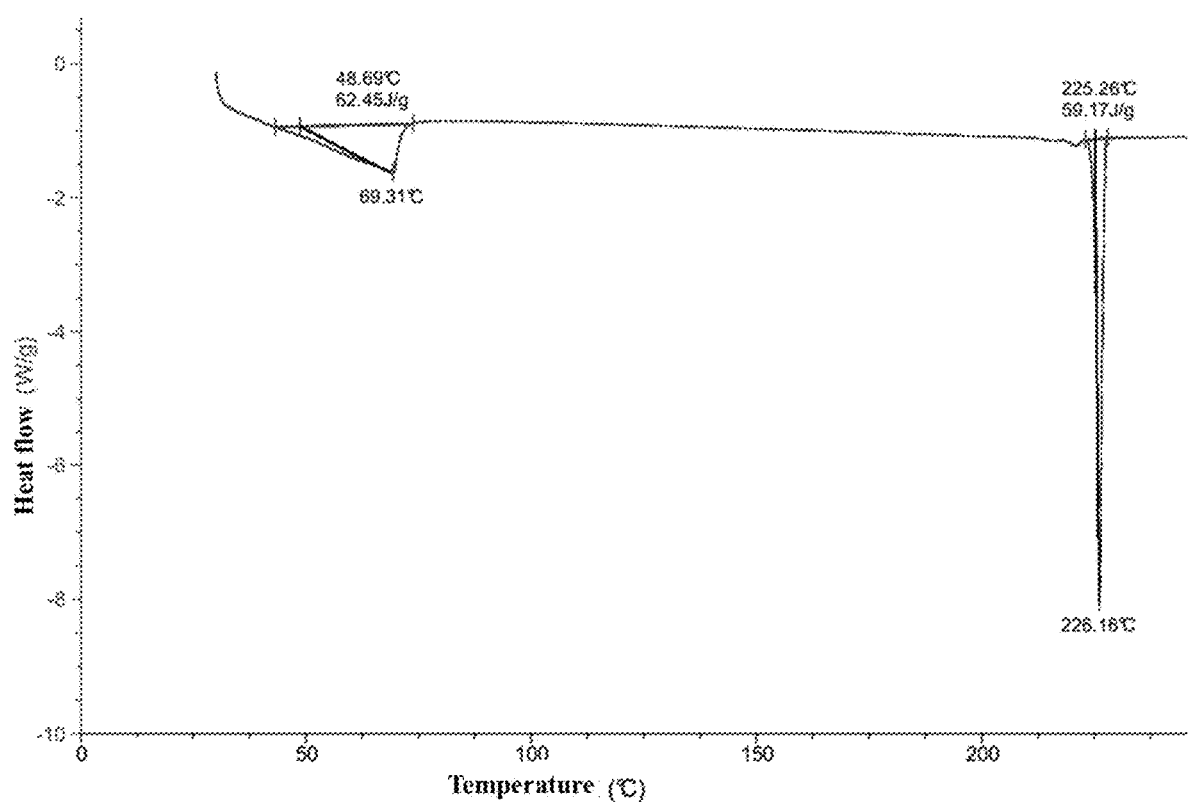
FIG. 17 shows the DSC pattern of the Crystal Form F of the compound of Formula (I)
Figure 18:
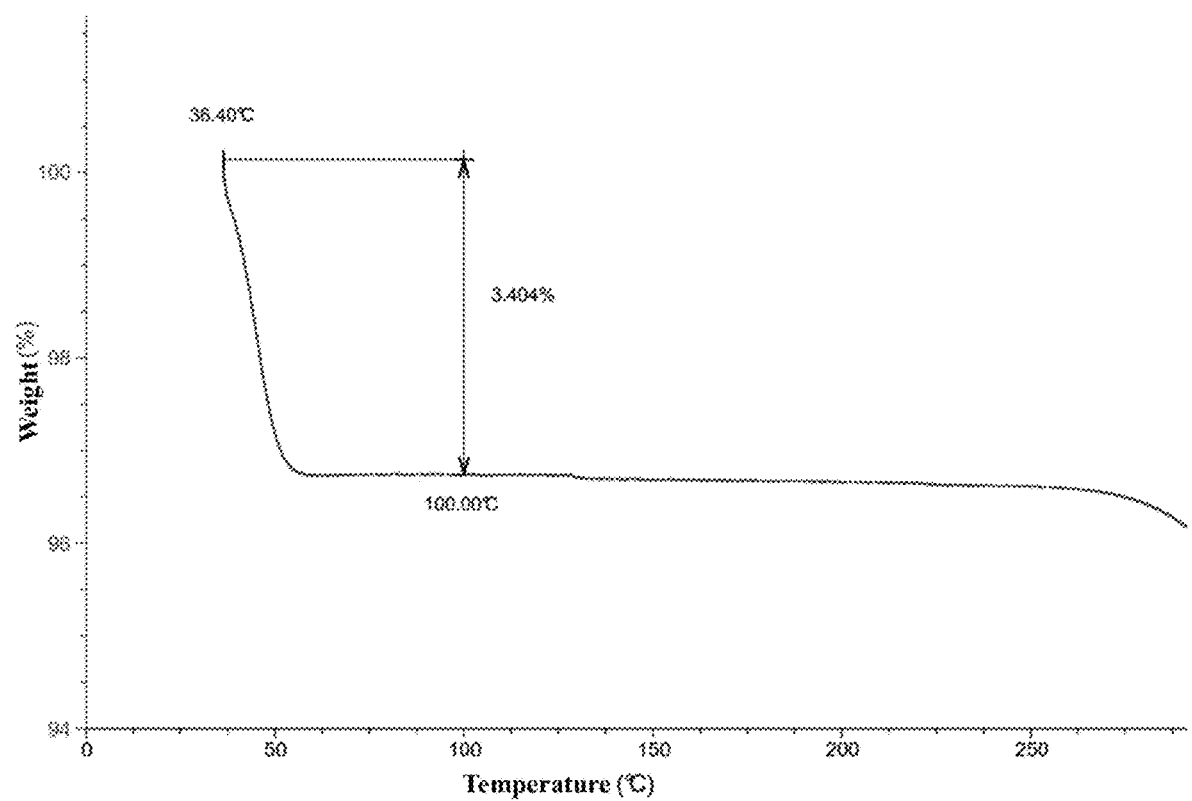
FIG. 18 shows the TGA pattern of the Crystal Form F of the compound of Formula (I).

23. The crystal form according to claim 1, being the Crystal Form F having an XRPD pattern as shown in FIG. 16.

24. The crystal form according to claim 1, being the Crystal Form F having a Differential Scanning calorimetry curve (DSC) having one onset point of endothermic peak at 48.69±3° C. and 225.26±3° C., respectively.

25. The crystal form according to claim 1, being the Crystal Form F having a Thermogravimetric Analysis curve (TGA), wherein the weight loss at 100±3° C. is 3.404%.

26. A method for treating a Wee1-related disease in a subject in need thereof, comprising administering to the subject an effective amount of the crystal form according to claim 1, wherein the Wee1-related disease is colon cancer or pancreatic cancer.

27. A process for preparing the Crystal Form F according to claim 1, comprising,
   (a) adding the compound of formula (I) into an alcohol solvent with stirring which is heated in an oil bath to 55~65° C.;
   (b) stirring at 47° C.-53° C. for 72 h;
   (c) stopping heating and keeping stirring with the temperature spontaneously lowered for 1 h to 27° C.;
   (d) allowing standing for 18 h, filtering and rinsing the filter cake with methanol; and
   (e) drying under vacuum at 60° C. for 48 h,
   wherein the alcohol solvent is methanol.

28. A pharmaceutical composition, comprising the crystal form according to claim 1.

* * * * *